(12) United States Patent
Nagatomo et al.

(10) Patent No.: US 12,346,493 B2
(45) Date of Patent: Jul. 1, 2025

(54) INFORMATION PROCESSING APPARATUS, ELECTRONIC DEVICE, INFORMATION PROCESSING SYSTEM, METHOD FOR PROCESSING INFORMATION, AND PROGRAM

(71) Applicant: KYOCERA Corporation, Kyoto (JP)

(72) Inventors: Takashi Nagatomo, Tokyo (JP); Edwardo Arata Yamamoto Murakami, Kawasaki (JP); Hideyuki Kimpara, Yokohama (JP); Takashi Suzuki, Sagamihara (JP); Mie Terasawa, Yokohama (JP); Martin Klinkigt, Tokyo (JP); Naoki Nishida, Yokohama (JP)

(73) Assignee: KYOCERA Corporation, Kyoto (JP)

( * ) Notice: Subject to any disclaimer, the term of this patent is extended or adjusted under 35 U.S.C. 154(b) by 0 days.

(21) Appl. No.: 18/564,941

(22) PCT Filed: May 25, 2022

(86) PCT No.: PCT/JP2022/021462
§ 371 (c)(1),
(2) Date: Nov. 28, 2023

(87) PCT Pub. No.: WO2022/250099
PCT Pub. Date: Dec. 1, 2022

(65) Prior Publication Data
US 2024/0241576 A1  Jul. 18, 2024

(30) Foreign Application Priority Data
May 28, 2021 (JP) .................................. 2021-090695

(51) Int. Cl.
*G06F 3/01* (2006.01)
*A61B 5/11* (2006.01)
*G01D 21/02* (2006.01)

(52) U.S. Cl.
CPC ............ *G06F 3/011* (2013.01); *A61B 5/1122* (2013.01); *G01D 21/02* (2013.01)

(58) Field of Classification Search
CPC ... A61B 5/1122; A61B 5/1114; A61B 5/0024; A61B 5/112; A61B 5/11; A61B 5/1123;
(Continued)

(56) References Cited

U.S. PATENT DOCUMENTS 11,675,418 B2  6/2023  Fukumoto et al.
11,726,549 B2  8/2023  Fukumoto et al.
(Continued)

FOREIGN PATENT DOCUMENTS

EP  3 782 548 A1  2/2021
JP  2016-150193 A  8/2016
(Continued)

OTHER PUBLICATIONS

ASICS Institute of Sport Science, "The Ultimate Walk", Kodansha Gendai Shinsho, Published in Sep. 2019, p. 92, 94, and 95.

*Primary Examiner* — Xuemei Zheng
(74) *Attorney, Agent, or Firm* — Studebaker Brackett PLLC

(57) ABSTRACT

An information processing apparatus includes a controller. The controller obtains sensor data indicating movement of body parts of a user from at least one sensor device attached to the body parts of the user. The controller estimates, on the basis of the obtained sensor data and learning models, states of body parts of the user other than the body parts of the user to which the at least one sensor device is attached.

17 Claims, 11 Drawing Sheets

| CASE | CASE C1 | CASE C2 | CASE C3 | CASE C4 | CASE C5 |
|---|---|---|---|---|---|
| SENSOR DEVICE | SENSOR DEVICE 10A | SENSOR DEVICE 10A SENSOR DEVICE 10D | SENSOR DEVICE 10A SENSOR DEVICE 10C | SENSOR DEVICE 10A SENSOR DEVICE 10B | SENSOR DEVICE 10A SENSOR DEVICE 10B SENSOR DEVICE 10D |
| (1) STATE OF HEAD | LEARNING MODEL 30A (90%, 84%) ◎ | SENSOR DEVICE 30F (91%, 83%) ◎ | SENSOR DEVICE 30K (92%, 85%) ◎ | SENSOR DEVICE 30P (94%, 87%) ◎ | SENSOR DEVICE 30U (95%, 88%) ◎ |
| (2) STATE OF ARMS | LEARNING MODEL 30B (83%, 66%) ○ | SENSOR DEVICE 30G (86%, 70%) ○ | SENSOR DEVICE 30L (84%, 67%) ○ | SENSOR DEVICE 30Q (88%, 73%) ○ | SENSOR DEVICE 30V (89%, 77%) ○ |
| (3) STATE OF TRUNK | LEARNING MODEL 30C (80%, 50%) △ | SENSOR DEVICE 30H (83%, 59%) △ | SENSOR DEVICE 30M (85%, 60%) ○ | SENSOR DEVICE 30R (82%, 59%) △ | SENSOR DEVICE 30W (82%, 60%) ○ |
| (4) STATE OF KNEES | LEARNING MODEL 30D (81%, 53%) △ | SENSOR DEVICE 30I (85%, 59%) △ | SENSOR DEVICE 30N (87%, 60%) ○ | SENSOR DEVICE 30S (79%, 55%) △ | SENSOR DEVICE 30X (89%, 64%) ○ |
| (5) STATE OF FEET | LEARNING MODEL 30E (85%, 63%) ○ | SENSOR DEVICE 30J (93%, 74%) ◎ | SENSOR DEVICE 30O (90%, 71%) ◎ | SENSOR DEVICE 30T (90%, 74%) ◎ | SENSOR DEVICE 30Y (90%, 74%) ◎ |

(58) Field of Classification Search
CPC ..... A61B 5/6802; A61B 5/681; A61B 5/6807;
A61B 5/6805; A61B 5/6813; A61B
5/6814; A61B 5/6823; A61B 5/6824;
A61B 5/6825; A61B 5/6828; A61B
5/6829; A61B 5/6822; A61B 5/4528;
A61B 2562/0219; G06F 3/011; G06F
3/012; A63F 13/428; A63F 13/212; G01D
21/02; G06V 40/23; G06N 20/00
See application file for complete search history.

(56) References Cited

U.S. PATENT DOCUMENTS

| | | | |
|---|---|---|---|
| 2015/0192413 A1* | 7/2015 | Bellusci | A61B 5/1114 |
| | | | 702/152 |
| 2016/0038088 A1* | 2/2016 | Lari | A61B 5/11 |
| | | | 600/595 |
| 2018/0070864 A1* | 3/2018 | Schuster | G16H 40/63 |
| 2020/0297243 A1 | 9/2020 | Katsuhara et al. | |
| 2021/0038974 A1 | 2/2021 | Ohashi | |
| 2021/0307652 A1* | 10/2021 | Lari | G09B 19/0038 |

FOREIGN PATENT DOCUMENTS

| | | |
|---|---|---|
| JP | 6741892 B1 | 8/2020 |
| JP | 2020-151267 A | 9/2020 |
| WO | 2017/026148 A1 | 2/2017 |
| WO | 2019/203188 A1 | 10/2019 |

* cited by examiner

FIG. 5

| (1) STATE OF HEAD | (2) STATE OF ARMS | (3) STATE OF TRUNK | (4) STATE OF KNEES | (5) STATE OF FEET |
|---|---|---|---|---|
| 5 | 4 | 3 | 1 | 2 |
| Good | Good | Average | Poor | Poor |

FIG. 6

| CASE | CASE C1 | CASE C2 | CASE C3 | CASE C4 | CASE C5 |
|---|---|---|---|---|---|
| SENSOR DEVICE | SENSOR DEVICE 10A | SENSOR DEVICE 10A SENSOR DEVICE 10D | SENSOR DEVICE 10A SENSOR DEVICE 10C | SENSOR DEVICE 10A SENSOR DEVICE 10B | SENSOR DEVICE 10A SENSOR DEVICE 10B SENSOR DEVICE 10D |
| (1) STATE OF HEAD | LEARNING MODEL 30A (90%, 84%) ◎ | SENSOR DEVICE 30F (91%, 83%) ◎ | SENSOR DEVICE 30K (92%, 85%) ◎ | SENSOR DEVICE 30P (94%, 87%) ◎ | SENSOR DEVICE 30U (95%, 88%) ◎ |
| (2) STATE OF ARMS | LEARNING MODEL 30B (83%, 66%) ○ | SENSOR DEVICE 30G (86%, 70%) ○ | SENSOR DEVICE 30L (84%, 67%) ○ | SENSOR DEVICE 30Q (88%, 73%) ○ | SENSOR DEVICE 30V (89%, 77%) ○ |
| (3) STATE OF TRUNK | LEARNING MODEL 30C (80%, 50%) △ | SENSOR DEVICE 30H (83%, 59%) △ | SENSOR DEVICE 30M (85%, 60%) ○ | SENSOR DEVICE 30R (82%, 59%) △ | SENSOR DEVICE 30W (82%, 60%) ○ |
| (4) STATE OF KNEES | LEARNING MODEL 30D (81%, 58%) △ | SENSOR DEVICE 30I (85%, 59%) △ | SENSOR DEVICE 30N (87%, 60%) ○ | SENSOR DEVICE 30S (79%, 55%) △ | SENSOR DEVICE 30X (89%, 64%) ○ |
| (5) STATE OF FEET | LEARNING MODEL 30E (85%, 68%) ○ | SENSOR DEVICE 30J (93%, 74%) ◎ | SENSOR DEVICE 30O (90%, 71%) ◎ | SENSOR DEVICE 30T (90%, 74%) ◎ | SENSOR DEVICE 30Y (90%, 74%) ◎ |

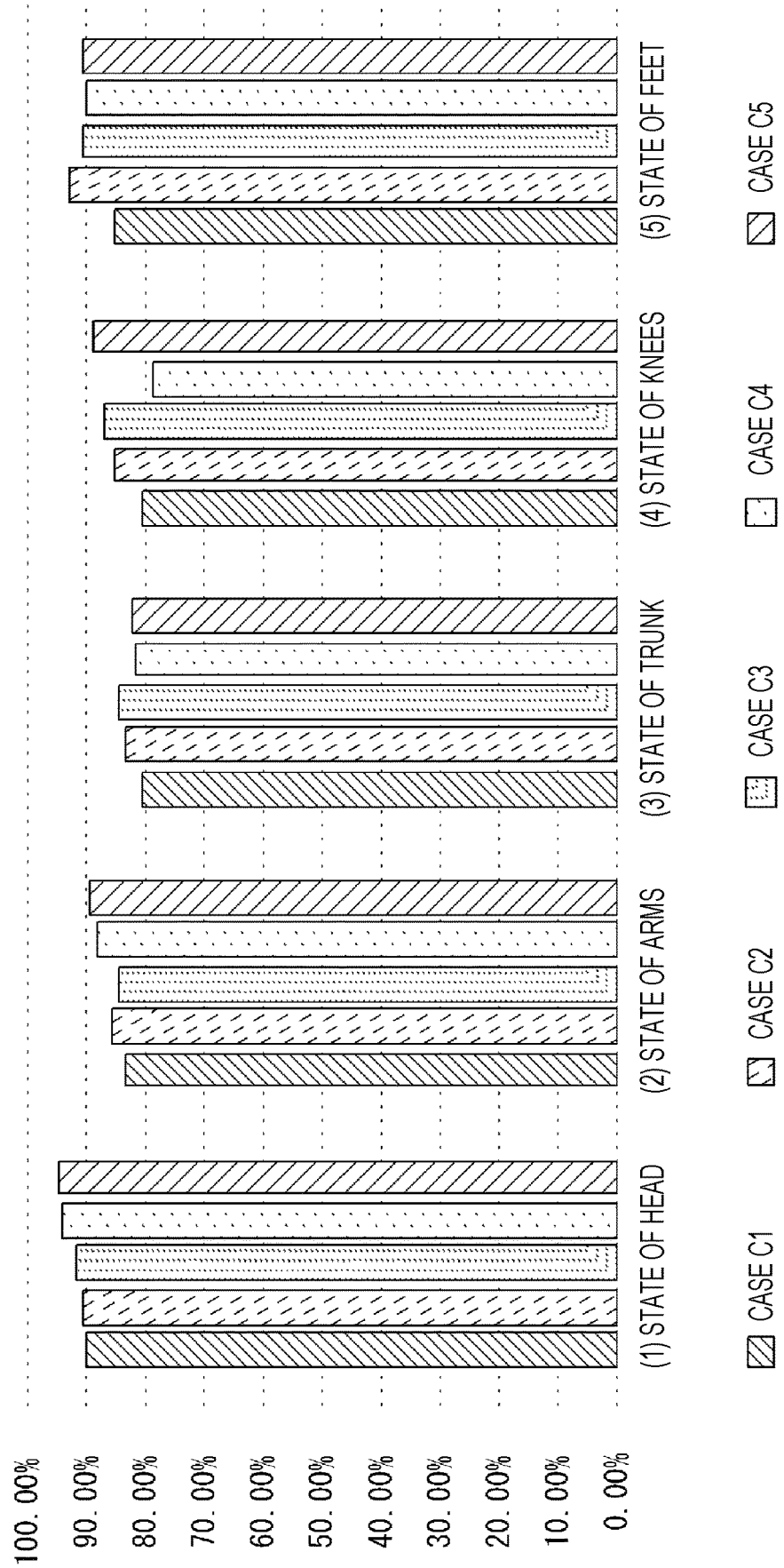

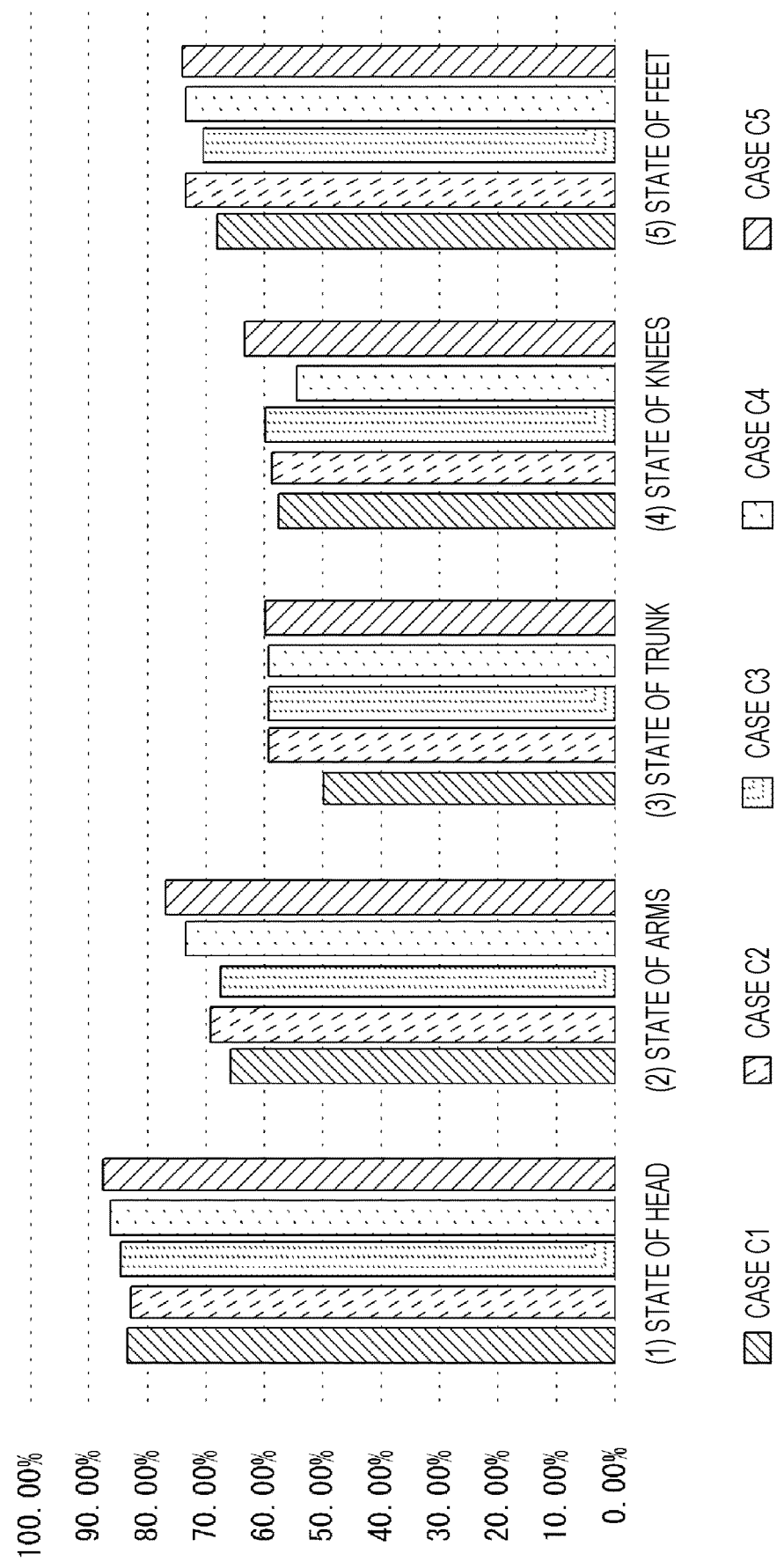

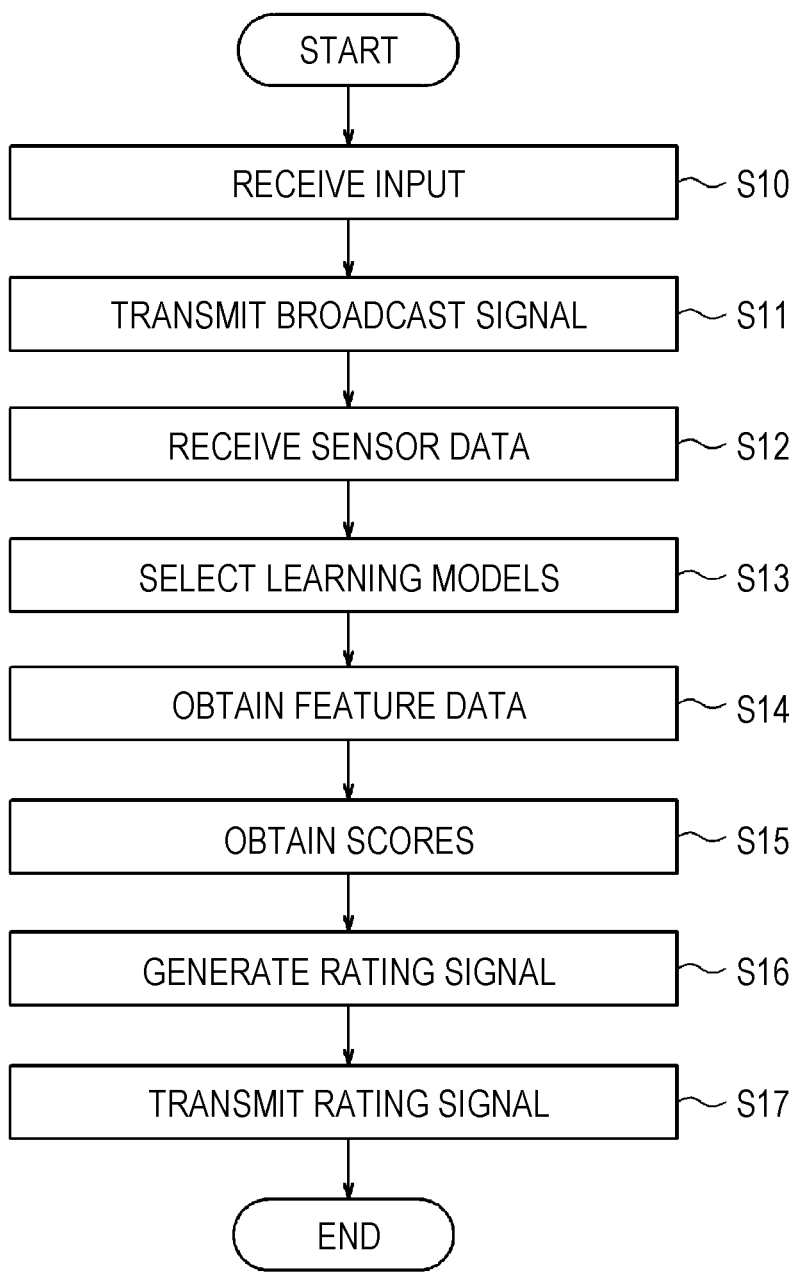

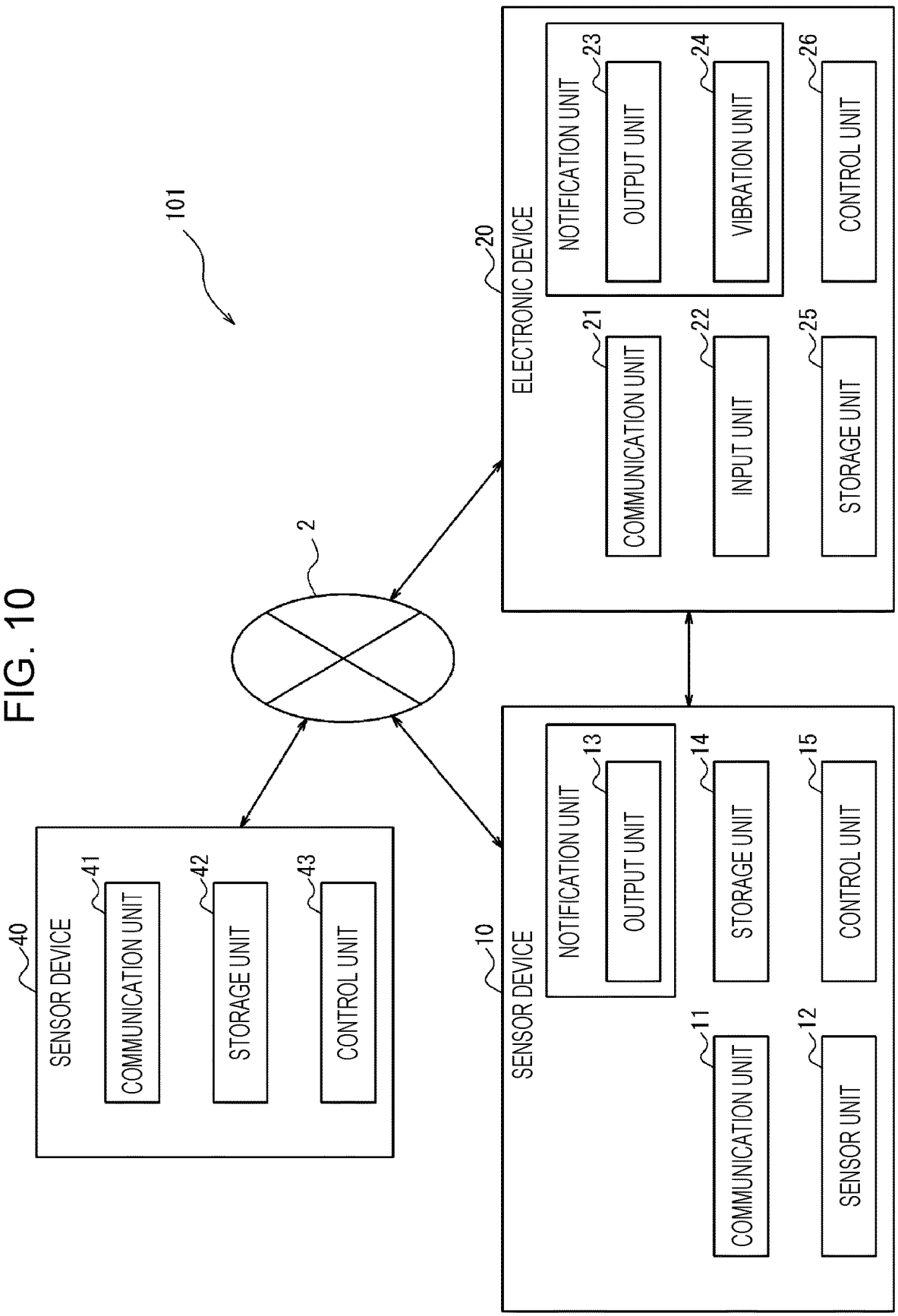

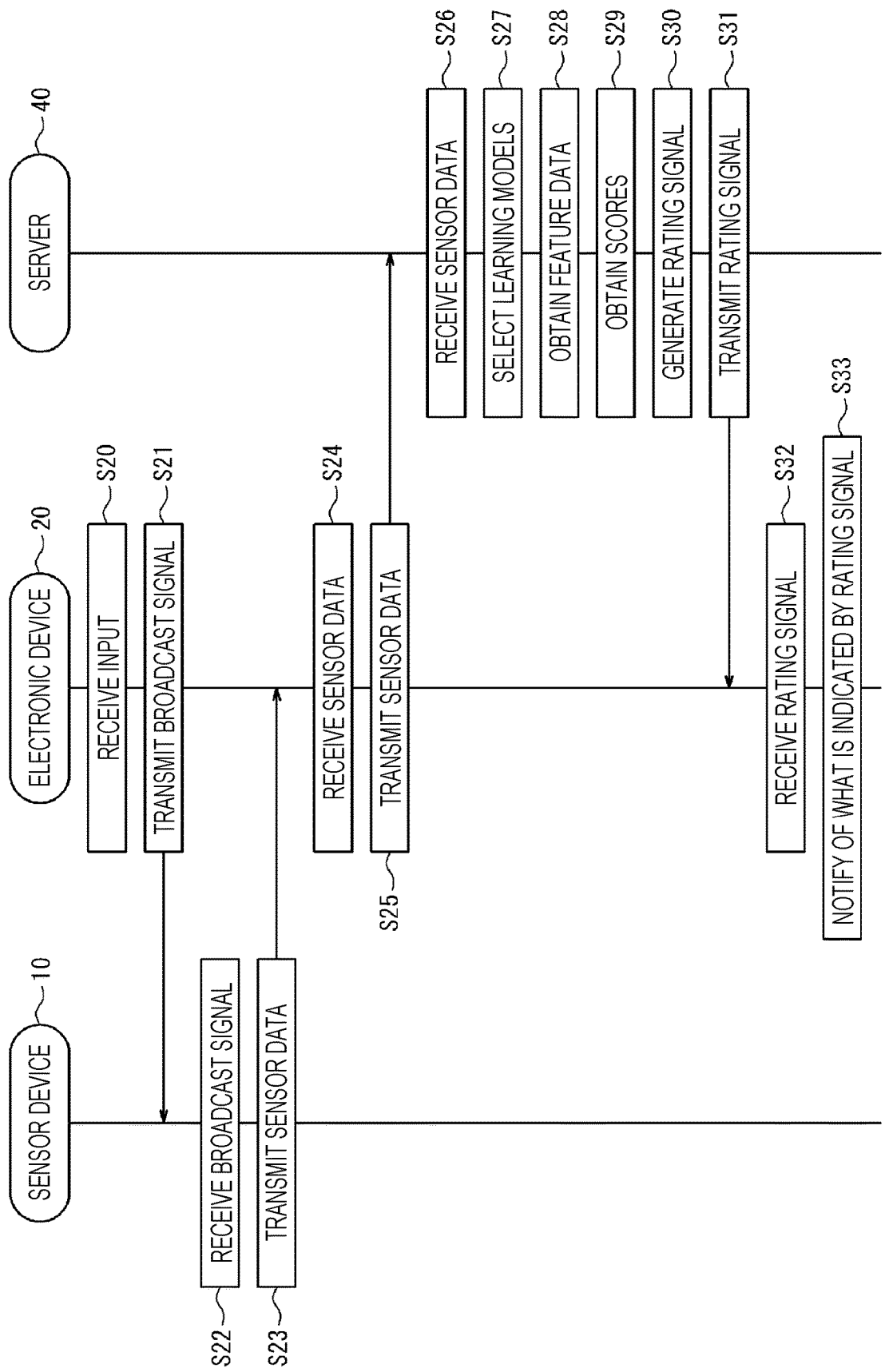

INFORMATION PROCESSING APPARATUS, ELECTRONIC DEVICE, INFORMATION PROCESSING SYSTEM, METHOD FOR PROCESSING INFORMATION, AND PROGRAM

CROSS-REFERENCE TO RELATED APPLICATIONS

The present application claims priority to Japanese Patent Application No. 2021-090695 filed in the Japan Patent Office on May 28, 2021, the entire contents of which are incorporated herein by reference.

TECHNICAL FIELD

The present disclosure relates to an information processing apparatus, an electronic device, an information processing system, a method for processing information, and a program.

BACKGROUND OF INVENTION

Techniques for estimating a person's walking state are known (e.g., Patent Literature 1). An exercise analysis apparatus described in Patent Literature 1 includes detection means attached to a person's body and analysis means. The analysis means analyzes a walking state and/or a running state on the basis of a signal from the detection means. As some of interpretations of good ways to walk, interpretations described in Non Patent Literature 1 are known.

CITATION LIST

Patent Literature

Patent Literature 1: Japanese Unexamined Patent Application Publication No. 2016-150193

Non Patent Literature

Non Patent Literature 1: ASICS Institute of Sport Science, "The Ultimate Walk", Kodansha Gendai Shinsho, Published in September 2019, p. 92, 94, and 95

SUMMARY

An information processing apparatus according to an embodiment of the present disclosure includes a controller. The controller obtains sensor data indicating movement of body parts of a user from at least one sensor device attached to the body parts of the user and estimates, on a basis of the obtained sensor data and learning models, states of body parts of the user other than the body parts of the user to which the at least one sensor device is attached.

An electronic device according to another embodiment of the present disclosure includes a notification unit. The notification notifies of information regarding the states of the body parts estimated by the information processing apparatus.

An information processing system according to another embodiment of the present disclosure includes at least one sensor device and an information processing apparatus. The at least one sensor device is attached to body parts of a user. The information processing apparatus obtains sensor data indicating movement of the body parts from the at least one sensor device and estimates, on a basis of the obtained sensor data and learning models, states of body parts of the user other than the body parts of the user to which the at least one sensor device is attached.

A method for processing information according to another embodiment of the present disclosure includes obtaining sensor data indicating movement of body parts of a user from at least one sensor device attached to the body parts of the user and estimating, on a basis of the obtained sensor data and learning models, states of body parts of the user other than the body parts of the user to which the at least one sensor device is attached.

A program according to another embodiment of the present disclosure causes a computer to execute a process including obtaining sensor data indicating movement of body parts of a user from at least one sensor device attached to the body parts of the user and estimating, on a basis of the obtained sensor data and learning models, states of body parts of the user other than the body parts of the user to which the at least one sensor device is attached.

BRIEF DESCRIPTION OF THE DRAWINGS

FIG. 5 is a diagram illustrating an example of scores according to the embodiment of the present disclosure.

FIG. 6 is a diagram illustrating an example of correspondences according to the embodiment of the present disclosure.

FIG. 7 is a graph illustrating precision of learning models.

FIG. 8 is a graph illustrating accuracy of the learning models.

FIG. 9 is a flowchart illustrating operations included in a rating process performed by an electronic device illustrated in FIG. 1.

FIG. 10 is a functional block diagram illustrating configuration of an information processing system according to another embodiment of the present disclosure.

FIG. 11 is a sequence diagram illustrating operations included in a rating process performed by the information processing system illustrated in FIG. 10.

DESCRIPTION OF EMBODIMENTS

Figure 1:
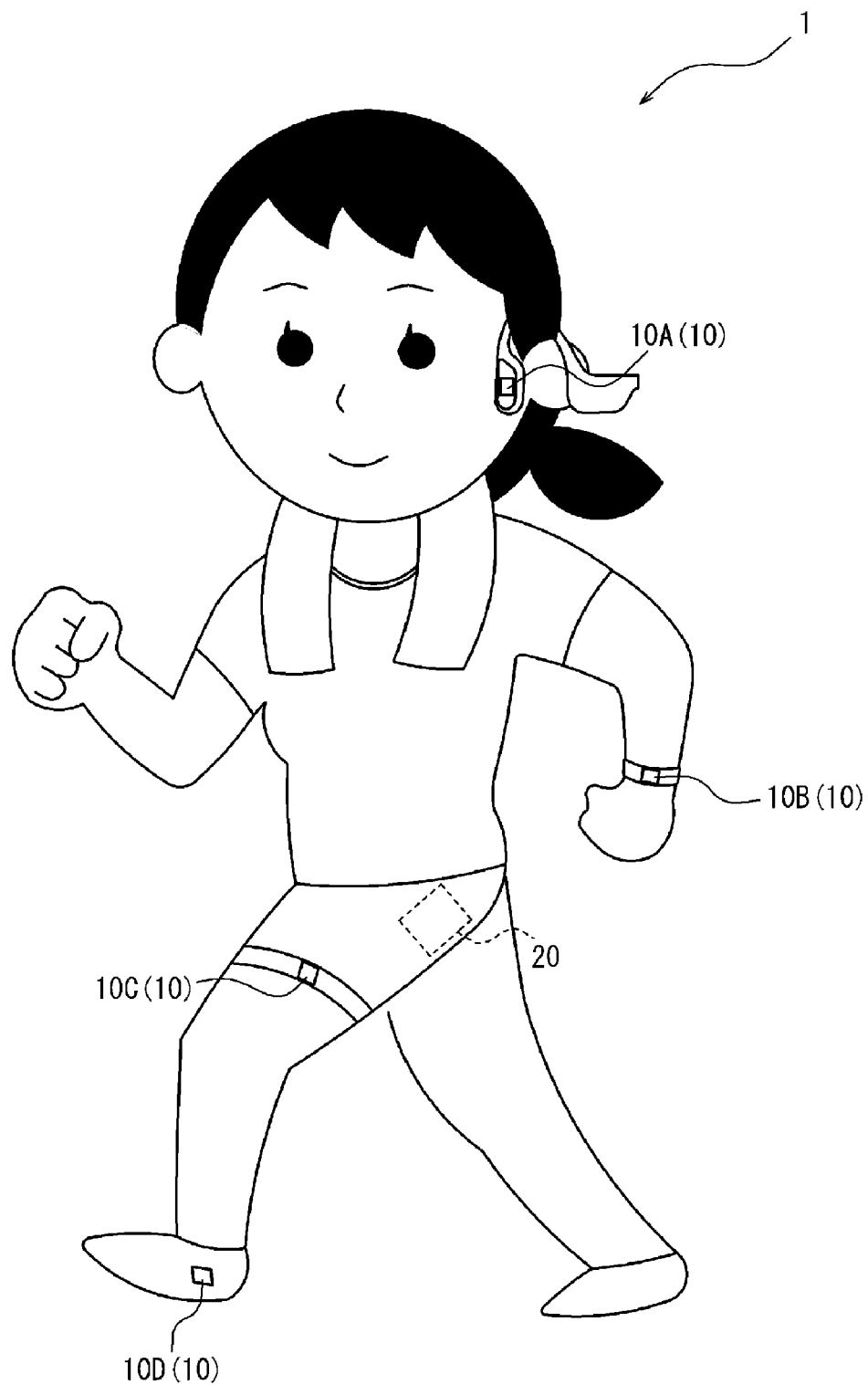
FIG. 1 is a diagram illustrating a schematic configuration of an information processing system according to an embodiment of the present disclosure.

A novel technique for estimating states of body parts of a user during walking is desired. According to the present disclosure, a novel technique for estimating states of body parts of a user during walking can be provided.

Embodiments of the present disclosure will be described hereinafter with reference to the drawings. Among components illustrated in the following drawings, the same components will be given the same reference numerals.

Configuration of System

An information processing system 1 illustrated in FIG. 1 can estimate states of some of a user's body parts during walking. The user can check, using the information processing system 1, whether the states of some of his/her body parts during walking are good or bad.

The information processing system 1 may be used for any purposes where states of body parts of a user during walking need to be detected. The information processing system 1 may be used to detect states of body parts of a user, for example, when the user walks as an exercise, practices walking as a model, practices footwork for climbing, or practices competitive walking.

The information processing system 1 includes a sensor device 10A, a sensor device 10B, a sensor device 10C, a sensor device 10D, and an electronic device 20. The information processing system 1, however, need not include all of the sensor device 10A, the sensor device 10B, the sensor device 10C, and the sensor device 10D. The information processing system 1 may include at least one selected from the group consisting of the sensor device 10A, the sensor device 10B, the sensor device 10C, and the sensor device 10D.

When the sensor devices 10A to 10D are not particularly distinguished from one another in the following description, these will be collectively referred to as "sensor devices 10".

The sensor devices 10 and the electronic device 20 are communicable with one another through a communication link. The communication link may be at least wired or wireless.

The sensor devices 10 are attached to some of the user's body parts. The sensor devices 10 detect sensor data indicating movement of the user's body parts to which the sensor devices 10 are attached. The sensor data is data in local coordinate systems.

Figure 2:
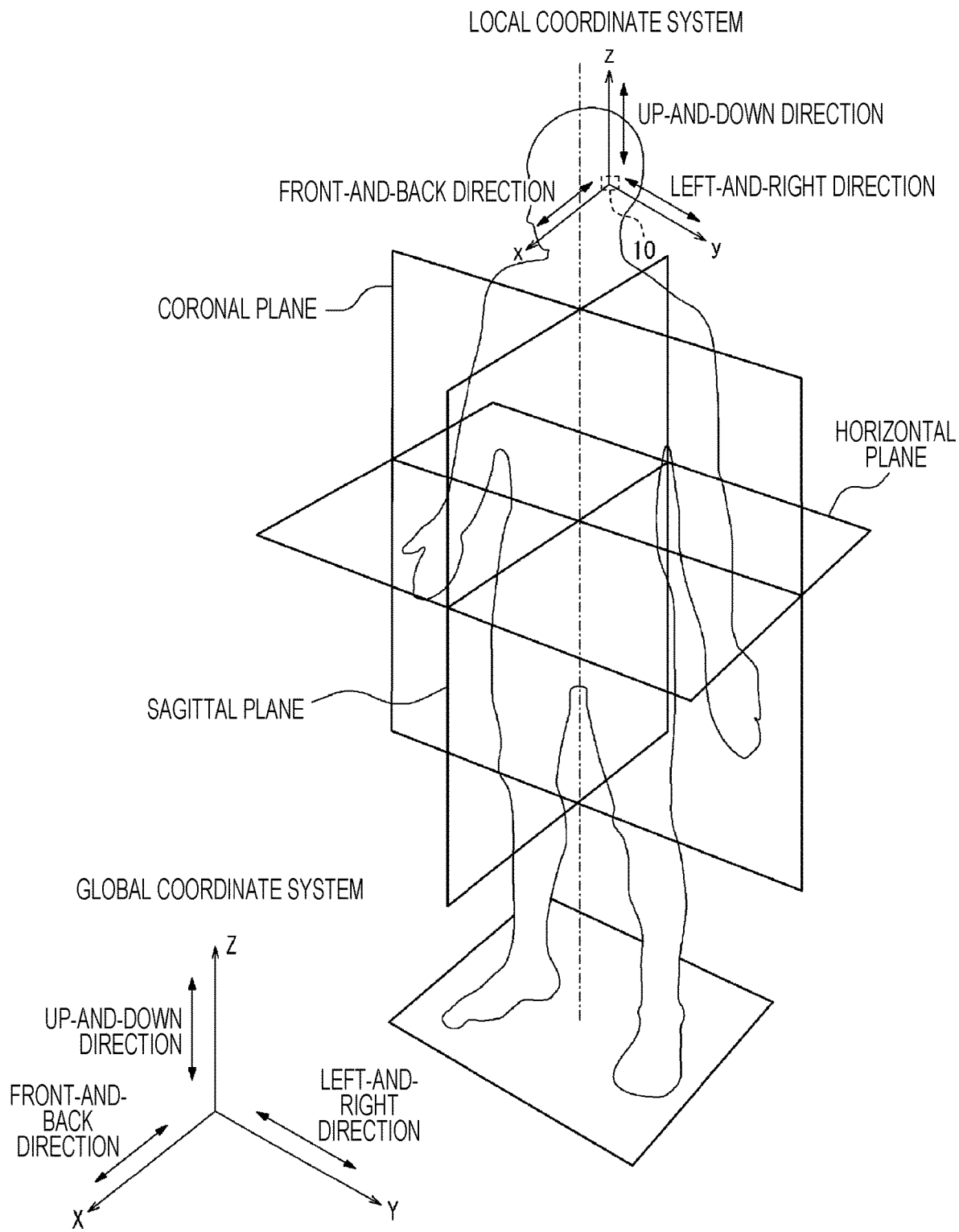
FIG. 2 is a diagram illustrating a local coordinate system and a global coordinate system.

As illustrated in FIG. 2, a local coordinate system is a coordinate system based on a position of a sensor device 10. In FIG. 2, a broken line indicates a position of the sensor device 10A as an example of the position of the sensor device 10. The local coordinate system is defined, for example, by an x-axis, a y-axis, and a z-axis. The x-axis, the y-axis, and the z-axis are perpendicular to one another. The x-axis is parallel to a front-and-back direction of the sensor device 10. The y-axis is parallel to a left-and-right direction of the sensor device 10. The z-axis is parallel to an up-and-down direction of the sensor device 10. A direction parallel to the x-axis of the local coordinate system will also be referred to as a "front-and-back direction of the local coordinate system". A direction parallel to the y-axis of the local coordinate system will also be referred to as a "left-and-right direction of the local coordinate system". A direction parallel to the z-axis of the local coordinate system will also be referred to as an "up-and-down direction of the local coordinate system".

As illustrated in FIG. 2, a global coordinate system is a coordinate system based on a position in a space where the user walks. The global coordinate system is defined, for example, by an X-axis, a Y-axis, and a Z-axis. The X-axis, the Y-axis, and the Z-axis are perpendicular to one another. The X-axis is parallel to a front-and-back direction of the user. The Y-axis is parallel to a left-and-right direction of the user. The Z-axis is parallel to an up-and-down direction of the user. A direction parallel to the X-axis of the global coordinate system will also be referred to as a "front-and-back direction of the global coordinate system". A direction parallel to the Y-axis of the local coordinate system will also be referred to as a "left-and-right direction of the global coordinate system". A direction parallel to the Z-axis of the global coordinate system will also be referred to as an "up-and-down direction of the global coordinate system". The front-and-back direction of the global coordinate system may also be referred to as the front-and-back direction of the user. The left-and-right direction of the global coordinate system may also be referred to as the left-and-right direction of the user. The up-and-down direction of the global coordinate system may also be referred to as the up-and-down direction of the user.

As illustrated in FIG. 2, a sagittal plane is a plane that symmetrically divides the user's body or a plane parallel to the plane that symmetrically divides the user's body. A coronal plane is a plane that divides the user's body into a ventral side and a dorsal side or a plane parallel to the plane that divides the user's body into the ventral side and the dorsal side. A horizontal plane is a plane that divides the user's body into an upper section and a lower section or a plane parallel to the plane that divides the user's body into the upper section and the lower section. The sagittal plane, the coronal plane, and the horizontal plane are perpendicular to one another.

As illustrated in FIG. 1, the sensor device 10A is attached to the user's head. For example, the sensor device 10A is attached to one of the user's ears. The sensor device 10A may be a wearable device. The sensor device 10A may be an earphone. The sensor device 10A may be included in an earphone. Alternatively, the sensor device 10A may be a device attachable to existing glasses, earphones, or another apparatus. The sensor device 10A may be attached to the user's head by any method. The sensor device 10A may be incorporated into a hair accessory such as a hair band or a hairpin, an earring, a helmet, a hat, a hearing aid, a denture, an implant, or the like and attached to the user's head.

The sensor device 10A may be attached to the user's head such that the front-and-back direction of the sensor device 10A matches the front-and-back direction of the user's head, the left-and-right direction of the sensor device 10A matches the left-and-right direction of the user's head, and the up-and-down direction of the sensor device 10 matches the up-and-down direction of the user's head. That is, the sensor device 10A may be attached to the user's head such that the x-axis of the local coordinate system based on the position of the sensor device 10A becomes parallel to the front-and-back direction of the user's head, the y-axis of the local coordinate system becomes parallel to the left-and-right direction of the user's head, and the z-axis of the local coordinate system becomes parallel to the up-and-down direction of the user's head. The front-and-back direction, the left-and-right direction, and the up-and-down direction of the sensor device 10A, however, need not necessarily match the front-and-back direction, the left-and-right direction, and the up-and-down direction of the user's head, respectively. In this case, an attitude of the sensor device 10A relative to the user's head may be initialized or made known as necessary. The relative attitude may be initialized or made known using information regarding a shape of a jig for attaching the sensor device 10A to the user's head or image information generated by capturing an image of the user's head to which the sensor device 10A is attached.

The sensor device 10A detects sensor data indicating movement of the user's head. The sensor data detected by the sensor device 10A includes, for example, data indicating at least one selected from the group consisting of velocity of the user's head, acceleration of the user's head, an angle of the user's head, angular velocity of the user's head, temperature of the user's head, and geomagnetism at a position of the user's head.

The sensor device 10B is attached to one of the user's forearms. For example, the sensor device 10B is attached to one of the user's wrists. The sensor device 10B may be a wearable device of a wristwatch type. The sensor device 10B may be attached to the user's forearm by any method. The sensor device 10B may be incorporated into a band, a bracelet, a friendship bracelet, a glove, a ring, a false nail, an artificial hand, or the like and attached to the user's forearm. The bracelet may be worn by the user for decorative purposes or to attach a locker key or other key to one of the user's wrists.

The sensor device 10B may be attached to the user's forearm such that the front-and-back direction of the sensor device 10B matches a front-and-back direction of a corresponding one of the user's wrists, the left-and-right direction of the sensor device 10B matches a left-and-right direction of the user's wrist, and the up-and-down direction of the sensor device 10B matches a rotation direction of the user's wrist. A rotation direction of a wrist is a direction in which the wrist twists and turns. That is, the sensor device 10B may be attached to the user's forearm such that the x-axis of the local coordinate system based on a position of the sensor device 10B becomes parallel to a front-and-back direction of a corresponding one of the user's wrists, the y-axis of the local coordinate system becomes parallel to a left-and-right direction of the user's wrist, and the z-axis of the local coordinate system becomes parallel to a rotation direction of the user's wrist.

The sensor device 10B detects sensor data indicating movement of the user's forearm. The sensor data detected by the sensor device 10B includes, for example, data indicating at least one selected from the group consisting of velocity of the user's forearm, acceleration of the user's forearm, an angle of the user's forearm, angular velocity of the user's forearm, temperature of the user's forearm, and geomagnetism at a position of the user's forearm.

The sensor device 10C is attached to one of the user's thighs. The sensor device 10C may be a wearable device. The sensor device 10C may be attached to the user's thigh by any method. The sensor device 10C may be attached to the user's thigh using a belt. The sensor device 10C may be put in a pocket of pants worn by the user near the user's thigh and attached to the user's thigh. The sensor device 10C may be incorporated into pants, an underwear, shorts, a supporter, a prosthetic leg, an implant, or the like and attached to the user's thigh.

The sensor device 10C may be attached to the user's thigh such that the front-and-back direction of the sensor device 10C matches a front-and-back direction of the user's thigh, the left-and-right direction of the sensor device 10C matches a left-and-right direction of the user's thigh, and the up-and-down direction of the sensor device 10C matches a rotation direction of the user's thigh. A rotation direction of a thigh is a direction in which the thigh twists and turns. That is, the sensor device 10C may be attached to the user's thigh such that the x-axis of the local coordinate system based on a position of the sensor device 10C becomes parallel to the front-and-back direction of the user's thigh, the y-axis of the local coordinate system becomes parallel to the left-and-right direction of the user's thigh, and the z-axis of the local coordinate system becomes parallel to the rotation direction of the user's thigh.

The sensor device 10C detects sensor data indicating movement of the user's thigh. The sensor data detected by the sensor device 10C includes, for example, data indicating at least one selected from the group consisting of velocity of the user's thigh, acceleration of the user's thigh, an angle of the user's thigh, angular velocity of the user's thigh, temperature of the user's thigh, and geomagnetism at a position of the user's thigh.

The sensor device 10D is attached to one of the user's feet. In the present embodiment, a foot refers to a part from an ankle to a toe of the user. The sensor device 10D may be a wearable device of a shoe type. The sensor device 10D may be attached to the user's foot by any method. The sensor device 10D may be provided for a shoe. The sensor device 10D may be incorporated into an anklet, a band, a friendship bracelet, a false nail, a tattoo sticker, a supporter, a cast, a sock, an insole, a prosthetic leg, a ring, an implant, or the like and attached to the user's foot.

The sensor device 10D may be attached to the user's foot such that the front-and-back direction of the sensor device 10D matches a front-and-back direction of the user's foot, the left-and-right direction of the sensor device 10D matches a left-and-right direction of the user's foot, and the up-and-down direction of the sensor device 10 matches an up-and-down direction of the user's foot. That is, the sensor device 10D may be attached to the user's foot such that the x-axis of the local coordinate system based on the position of the sensor device 10D becomes parallel to the front-and-back direction of the user's foot, the y-axis of the local coordinate system becomes parallel to the left-and-right direction of the user's foot, and the z-axis of the local coordinate system becomes parallel to the up-and-down direction of the user's foot.

The sensor device 10D detects sensor data indicating movement of the user's foot. The sensor data detected by the sensor device 10D includes, for example, data indicating at least one selected from the group consisting of velocity of the user's foot, acceleration of the user's foot, an angle of the user's foot, angular velocity of the user's foot, temperature of the user's foot, and geomagnetism at a position of the user's foot.

The electronic device 20 is carried, for example, by a user during walking. The electronic device 20 functions as an information processing apparatus and is capable of estimating states of some of the user's body parts on the basis of sensor data detected by the sensor device 10. When estimating states of body parts of the user, the electronic device 20 determines ratings of the states of the body parts of the user in the present embodiment. The electronic device 20 is, for example, a mobile device such as a mobile phone, a smartphone, or a tablet.

Figure 3:
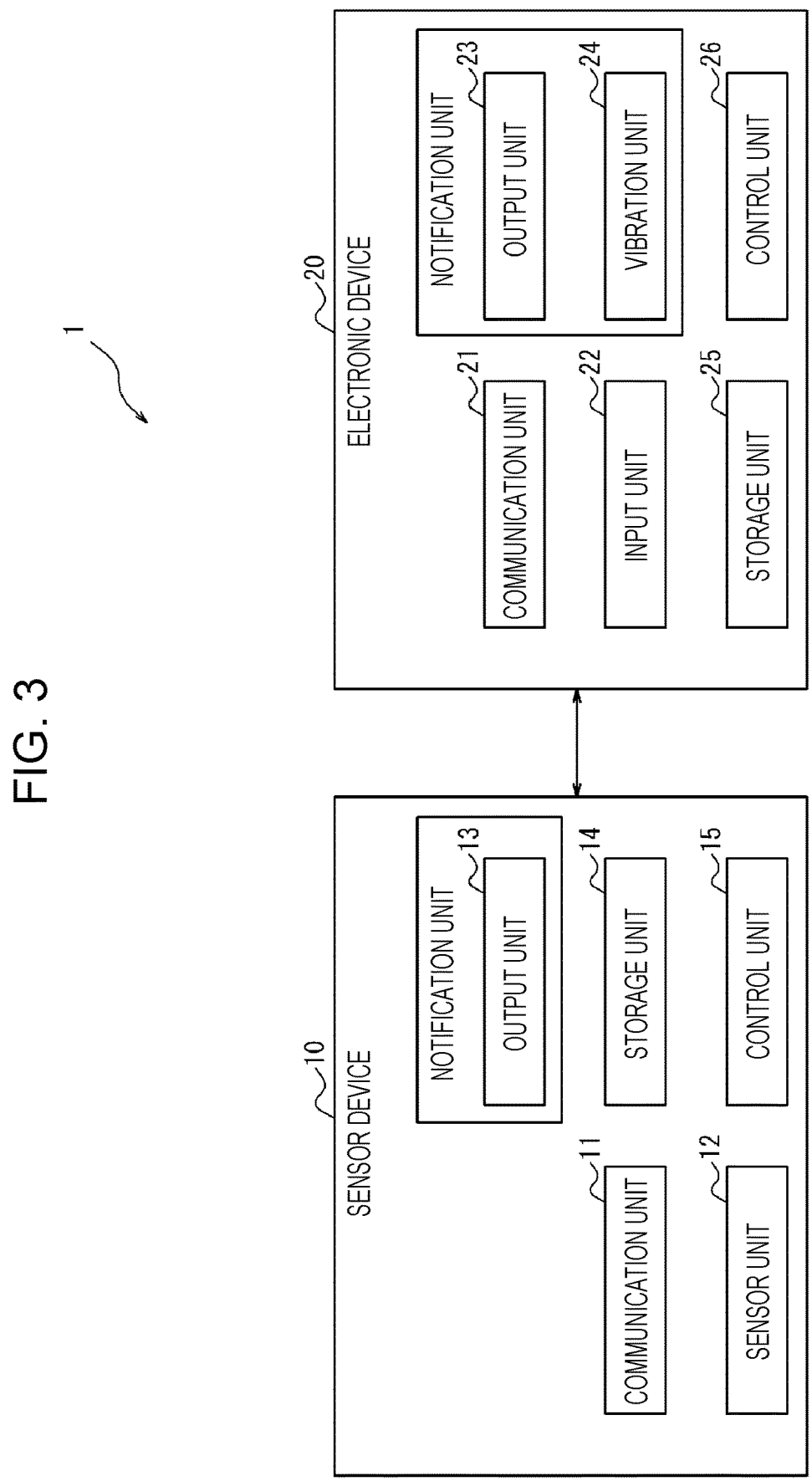
FIG. 3 is a functional block diagram illustrating configuration of the information processing system illustrated in FIG. 1.

As illustrated in FIG. 3, the sensor device 10 includes at least a communication unit 11 and a sensor unit 12. The sensor device 10 may also include a notification unit that notifies of information, a storage unit 14, and a control unit 15. In the present embodiment, the notification unit is an output unit 13. The notification unit, however, is not limited to the output unit 13. The sensor device 10C and the sensor device 10D need not include an output unit 13.

The communication unit 11 includes at least one communication module communicable with the electronic device 20 through the communication link. The communication module complies with a standard for the communication link. The standard for the communication link is, for example, a short distance wireless communication standard such as Bluetooth (registered trademark), Wi-Fi (registered trademark), infrared light, or NFC (near-field communication).

The sensor unit 12 includes any sensor(s) corresponding to sensor data to be detected by the sensor device 10. The sensor unit 12 includes, for example, at least one selected from the group consisting of a three-axis motion sensor, a three-axis acceleration sensor, a three-axis velocity sensor, a three-axis gyro sensor, a three-axis geomagnetic sensor, a temperature sensor, an air pressure sensor, and a camera.

When the sensor unit 12 includes a camera, the camera can detect movement of a body part of the user by analyzing an image generated by capturing an image of the body part.

When the sensor unit 12 includes an acceleration sensor and a geomagnetic sensor, data detected by the acceleration sensor and the geomagnetic sensor may be used to calculate an initial angle of a body part to be detected by the sensor device 10. The data detected by the acceleration sensor and the geomagnetic sensor may be used to correct data indicating an angle detected by the sensor device 10.

When the sensor unit 12 includes a gyro sensor, the angle of the body part to be detected by the sensor device 10 may be calculated by time-integrating angular velocity detected by the gyro sensor.

When the sensor unit 12 includes an air pressure sensor, data detected by the air pressure sensor may be used when a control unit 26 of the electronic device 20, which will be described later, determines ratings of states of body parts of the user.

The output unit 13 is capable of outputting data. The output unit 13 includes at least one output interface capable of outputting data. The output interface is, for example, a display, a speaker, or the like. The display is, for example, an LCD (liquid crystal display), an organic EL (electro luminescence) display, or the like.

When the output unit 13 is included in the sensor device 10A, the output unit 13 may include a speaker. When the output unit 13 is included in the sensor device 10B, the output unit 13 may include a display.

The storage unit 14 includes at least one semiconductor memory, at least one magnetic memory, at least one optical memory, or a combination of at least two of these. The semiconductor memory is, for example, a RAM (random-access memory), a ROM (read-only memory), or the like. The RAM is, for example, an SRAM (static random-access memory), a DRAM (dynamic random-access memory), or the like. The ROM is, for example, an EEPROM (electrically erasable programmable read-only memory) or the like. The storage unit 14 may function as a main storage device, an auxiliary storage device, or a cache memory. The storage unit 14 stores data used for the operation of the sensor device 10 and data obtained as a result of the operation of the sensor device 10. For example, the storage unit 14 stores a system program, application programs, embedded software, and the like.

The control unit 15 includes at least one processor, at least one dedicated circuit, or a combination of these. The processor is a general-purpose processor such as a CPU (central processing unit) or a GPU (graphics processing unit) or a dedicated processor specialized in a certain type of processing. The dedicated circuit is, for example, an FPGA (field-programmable gate array), an ASIC (application-specific integrated circuit), or the like. The control unit 15 performs processing relating to the operation of the sensor device 10 while controlling the components of the sensor device 10.

The control unit 15 receives a signal for requesting a start of data detection from the electronic device 20 using the communication unit 11. Upon receiving the signal, the control unit 15 starts the data detection. For example, the control unit 15 obtains data detected by the sensor unit 12 from the sensor unit 12. The control unit 15 transmits, using the communication unit 11, the obtained data to the electronic device 20 as sensor data. The electronic device 20 transmits the signal for requesting a start of data detection to a plurality of sensor devices 10 as a broadcast signal. Since the signal for requesting a start of data detection is transmitted to a plurality of sensor devices 10 as a broadcast signal, the plurality of sensor devices 10 can simultaneously start the data detection.

The control unit 15 obtains data from the sensor unit 12 and transmits the obtained data as sensor data using the communication unit 11 at preset time intervals. The time intervals may be set on the basis of walking speed of a general user or the like. The time intervals may be the same between the plurality of sensor devices 10. When the time intervals are the same between the plurality of sensor devices 10, timing of the data detection can be synchronized between the plurality of sensor devices 10.

As illustrated in FIG. 3, the electronic device 20 includes a communication unit 21, an input unit 22, a notification unit that notifies of information, a storage unit 25, and the control unit 26. In the present embodiment, the notification unit is an output unit 23 and a vibration unit 24. The notification unit, however, is not limited to the output unit 23 and the vibration unit 24. The output unit 23 and the vibration unit 24 may be incorporated into the electronic device 20 or provided near the sensor device 10B, 10C, or 10D.

The communication unit 21 includes at least one communication module communicable with the sensor devices 10 through the communication link. The communication module is at least one communication module that complies with the standard for the communication link. The standard for the communication link is, for example, a short distance wireless communication standard such as Bluetooth (registered trademark), Wi-Fi (registered trademark), infrared light, or NFC.

The communication unit 21 may also include at least one communication module connectable to a network 2 illustrated in FIG. 10, which will be described later. The communication module is, for example, a communication module that complies with a mobile communication standard such as LTE (long-term evolution), 4G (4th generation), or 5G (5th generation).

The input unit 22 is capable of receiving inputs from the user. The input unit 22 includes at least one input interface capable of receiving inputs from the user. The input interface is, for example, physical keys, capacitive keys, a pointing device, a touch screen integrated with a display, a microphone, or the like.

The output unit 23 is capable of outputting data. The output unit 23 includes at least one output interface capable of outputting data. The output interface is, for example, a display, a speaker, or the like. The display is, for example, an LCD, an organic EL display, or the like.

The vibration unit 24 is capable of vibrating the electronic device 20. The vibration unit 24 includes a vibration element. The vibration element is, for example, a piezoelectric element or the like.

The storage unit 25 includes at least one semiconductor memory, at least one magnetic memory, at least one optical memory, or a combination of at least two of these. The semiconductor memory is, for example, a RAM, a ROM, or the like. The RAM is, for example, an SRAM, a DRAM, or the like. The ROM is, for example, an EEPROM or the like. The storage unit 25 may function as a main storage device, an auxiliary storage device, or a cache memory. The storage unit 25 stores data used for the operation of the electronic device 20 and data obtained as a result of the operation of the electronic device 20. For example, the storage unit 25 stores a system program, application programs, embedded software, and the like. For example, the storage unit 25 stores learning models that will be described later, correspondences such as ones illustrated in FIG. 6, which will be described later, and the like.

The control unit 26 includes at least one processor, at least one dedicated circuit, or a combination of these. The processor is a general-purpose processor such as a CPU or a GPU or a dedicated processor specialized in a certain type of processing. The dedicated circuit is, for example, an FPGA, an ASIC, or the like. The control unit 26 performs processing relating to the operation of the electronic device 20 while controlling the components of the electronic device 20.

The control unit 26 receives, using the input unit 22, an input for requesting execution of walking rating. The input is an input for causing the electronic device 20 to perform a determination process for determining ratings of states of body parts. The input is made, for example, by the user who wears the sensor devices 10 from the input unit 22. The user makes the input from the input unit 22, for example, before starting to walk. Upon receiving the input from the input unit 22, the control unit 26 transmits, using the communication unit 21, a signal for requesting a start of data detection to a plurality of sensor devices 10 as a broadcast signal. After the signal for requesting a start of data detection is transmitted to the plurality of sensor devices 10, at least one of the sensor devices 10 transmits sensor data to the electronic device 20.

The control unit 26 receives, using the communication unit 21, sensor data from at least one of the plurality of sensor devices 10. The control unit 26 receives the sensor data from the sensor device(s) 10 to obtain the sensor data from the sensor device(s) 10. As described later, the control unit 26 determines ratings of states of body parts of the user on the basis of the obtained sensor data and the learning models. How states of body parts are rated may be set on the basis of interpretations of ways to walk generally considered good. The interpretations of ways to walk generally considered good are, for example, ones described in "ASICS Institute of Sport Science, "The Ultimate Walk", Kodansha Gendai Shinsho, Published in September 2019, p. 92, 94, and 95". Before describing details of the process for determining ratings performed by the control unit 26, an example of the interpretations of ways to walk generally considered good and how states of body parts are rated will be described. The control unit 26 may determine a rating of at least one selected from the group consisting of (1) state of head, (2) state of arms, (3) state of trunk, (4) state of knees, and (5) state of feet, which will be described hereinafter.

(1) State of Head

A rating of a state of the head may be determined.

In a general interpretation, a user's body should sway as little as possible during walking. When the sway of a user's body during walking is small, the sway of the user's head during walking is smaller than when the sway of the user's body during walking is large. When the sway of the user's head during walking is small, therefore, a higher rating may be determined for the state of the head than when the sway of the user's head during walking is large.

When a user's chin is pulled in during walking, the user's head sways less than when the user's chin is not pulled in during walking. When a user's chin is pulled in during walking, therefore, a higher rating may be determined for the state of the head than when the user's chin is not pulled in during walking.

When a user's gaze is directed farther away during walking, the user's head sways less than when the user's gaze is directed closer during walking. When a user's gaze is directed farther away during walking, therefore, a higher rating may be determined for the state of the head than when the user's gaze is directed closer to the user while walking.

(2) State of Arms

A rating of a state of the arms may be determined.

A state where a user swings his/her arms wide is generally interpreted to be a good state of the arms during walking. When the user swings his/her arms wide during walking, therefore, a higher rating may be determined for the state of the arms than when the user swings his/her arms small during walking.

A state where a user's arms are pulled in a backward direction of the user is generally interpreted to be a good state of the arms during walking. When a user's arms are pulled in backward during walking, therefore, a higher rating may be determined for the state of the arms than when the user's arms are not pulled in backward during walking.

(3) State of Trunk

A rating of a state of the trunk may be determined.

A state where a user's shoulders are open and the user's back muscles are extended is generally interpreted to be a good state of the trunk during walking. When the user's shoulders are open and the user's back muscles are extended, therefore, a higher rating may be determined for the state of the trunk than when the user's shoulders are closed and the user's back muscles are bent.

A state where a user's pelvis is erect and the user's waist is extended is generally interpreted to be a good state of the trunk during walking. When the user's pelvis is erect and the user's waist is extended, therefore, a higher rating may be determined for the state of the trunk than when the user's pelvis is not erect and the user's waist is bent.

(4) State of Knees

A rating of a state of the knees may be determined.

A state where a user's knees are not bent is generally interpreted to be a good state of the knees during walking. When the user's knees are not bent during walking, therefore, a higher rating may be determined for the state of the knees than when the user's knees are bent during walking.

(5) State of Feet

A rating of a state of the feet may be determined.

In a general interpretation, a user's stride during walking should be as long as possible. When a user's stride is long during walking, therefore, a higher rating may be determined for the state of the feet than when the user's stride is short during walking.

[Process for Determining Ratings]

The control unit 26 determines ratings of states of body parts of the user on the basis of sensor data and learning models. The learning models have been subjected to machine learning such that when sensor data or feature data is input, information regarding ratings of states of certain body parts of the user is output. That is, the control unit 26 determines ratings of states of body parts of the user by inputting sensor data or feature data to the learning models and obtaining, from the leaning models, information regarding the ratings of the states of the body parts of the user. The feature data is data indicating features of movement of body parts of the user to which the sensor devices 10 are attached. The control unit 26 obtains the feature data from sensor data. An example of the feature data will be described later. Here, the learning models may be subjected to machine learning such that when sensor data or feature data is input, information regarding ratings of states of body parts of the user other than those to which the sensor devices 10 are attached. This is because a plurality of body parts of the user affects each other during walking. With such learning models, the control unit 26 can determine ratings of states of body parts of the user other than those to which the sensor devices 10 are attached. With such learning models, the control unit 26 can determine ratings of more body parts of the user than those to which the sensor devices 10 are attached.

The learning models according to the present embodiment have been subjected to machine learning such that when feature data is input, scores are output as information regarding ratings of states of certain body parts. The scores indicate the ratings of the states of the certain body parts. The higher the scores, the higher the ratings of the states of the certain body parts corresponding to the scores. The control unit 26 obtains scores from the learning models and determines ratings of states of certain body parts corresponding to the scores.

An example of feature data input to a learning model will be described hereinafter.

The feature data may be data indicating a statistic value of sensor data. When the feature data is a statistic value of sensor data, the feature data can represent features of movement of a body part. For example, the feature data is a maximum, a minimum, an average, or a variance of sensor data in a certain period of time. The certain period of time is, for example, the user's gait cycle or a part of the user's gait cycle. The gait cycle is, for example, a period that begins when one of the user's feet comes into contact with the ground and that ends when the user's foot comes into contact with the ground again. The part of the user's gait cycle is, for example, a stance phase, a swing phase, or the like. The stance phase is, for example, a period that begins when one of the user's feet comes into contact with the ground and that ends when the user's foot leaves the ground. The swing phase is, for example, a period that begins when one of the user's feet leaves the ground and that ends when the user's foot comes into contact with the ground. The control unit 26 may detect the user's gait cycle or the part of the user's gait cycle by analyzing sensor data. The control unit 26 may obtain feature data from sensor data by performing arithmetic processing on the sensor data.

The feature data may be sensor data at a certain time. When the feature data is sensor data at a certain time, the feature data can represent features of movement of a body part. For example, the feature data is sensor data at a landing time of the user. The landing time is when one of the user's feet comes into contact with the ground. The control unit 26 may detect the landing time by analyzing sensor data.

The feature data may be data in any coordinate system. The feature data may be data in a local coordinate system or data in a global coordinate system. When the feature data is data in a global coordinate system, the control unit 26 obtains feature data in the global coordinate system by performing a coordinate transformation on sensor data in a global coordinate system.

Figure 4:
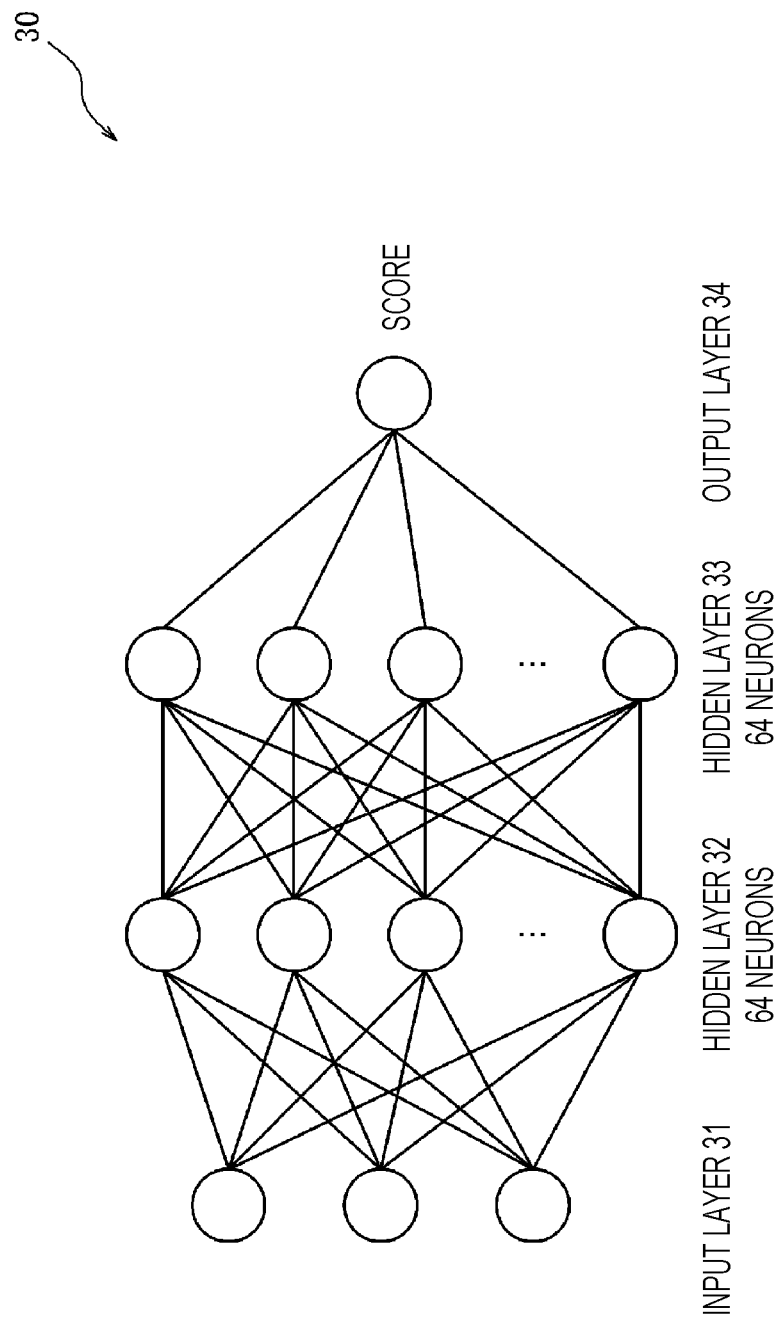
FIG. 4 is a diagram illustrating a schematic configuration of a learning model according to the embodiment of the present disclosure.

An example of a learning model will be described with reference to FIG. 4. A learning model 30 illustrated in FIG. 4 is a learning model of a neural network. The learning model 30 includes an input layer 31, a hidden layer 32, a hidden layer 33, and an output layer 34.

When three pieces of feature data are input from the input layer 31, the learning model 30 outputs one score from the output layer 34.

The input layer 31 includes three neurons. Feature data is input to each of the three neurons in the input layer 31. The hidden layer 32 and the hidden layer 33 each include 64 neurons. The output layer 34 includes one neuron. The neuron in the output layer 34 outputs a score. Neurons in two adjacent layers among the input layer 31, the hidden layer 32, the hidden layer 33, and the output layer 34 are connected to each other. In training of the learning model 30, weight coefficients, which correspond to connection strength between neurons, are adjusted.

The number of neurons included in the input layer 31, the hidden layer 32, the hidden layer 33, and the output layer 34 may be adjusted in accordance with the number of pieces of feature data used.

FIG. 5 illustrates an example of scores according to the embodiment of the present disclosure. As described above, the control unit 26 obtains scores such as those illustrated in FIG. 5 by inputting feature data to the learning models. In FIG. 5, the control unit 26 obtains scores of (1) state of head, (2) state of arms, (3) state of trunk, (4) state of knees, and (5) state of feet using five learning models.

In FIG. 5, the scores range from 1 to 5. The control unit 26 obtains a score of 5 as a rating of (1) state of head. The control unit 26 obtains a score of 4 as a rating of (2) state of arms. The control unit 26 obtains a score of 3 as a rating of (3) state of trunk. The control unit 26 obtains a score of 1 as a rating of (4) state of knees. The control unit 26 obtains a score of 2 as a rating of (5) state of feet.

[Process for Generating Rating Signal]

After determining a rating of a state of a body part of the user, the control unit 26 may generate a rating signal based on the determined rating. If determining a plurality of ratings, the control unit 26 may generate a rating signal based on at least one of the determined ratings. If a determined rating is higher than a rating threshold, the rating signal may be a signal indicating a praise for the user. If a determined rating is lower than the rating threshold, the rating signal may be a signal indicating advice for the user. The rating threshold may be set on the basis of an average of ratings for general users or the like. When a learning model is used, the rating threshold may be an average of scores for general users. The praise for the user and the advice may be set on the basis of the above-described interpretations of ways to walk generally considered good.

In FIG. 5, the rating threshold is a score of 3. In FIG. 5, "good" indicates that a rating is higher than the rating threshold. "Poor" indicates that a rating is lower than the rating threshold. "Average" indicates that a rating is equal to the rating threshold.

In FIG. 5, ratings of (1) state of head and (2) state of arms are higher than the rating threshold. The control unit 26 generates a signal indicating a praise for the user for each of (1) state of head and (2) state of arms as a rating signal. For example, the control unit 26 generates a signal indicating that a state of the user's head is good because the user's head sways little as a rating signal for (1) state of head. For example, the control unit 26 generates a signal indicating that the state of the user's arms is good because the user is swinging his/her arms wide and pulling in his/her arms backward as a rating signal for (2) state of arms.

In FIG. 5, ratings of (4) state of knees and (5) state of feet are lower than the rating threshold. The control unit 26 generates a signal indicating advice for the user for each of (4) state of knees and (5) state of feet as a rating signal. For example, the control unit 26 generates a signal for advising the user not to bent his/her knees as a rating signal for (4) state of knees. For example, the control unit 26 generates a signal for advising the user to increase his/her stride as a rating signal for (5) state of feet.

The control unit 26 may transmit a generated rating signal to an external device using the communication unit 21. The control unit 26 may transmit the rating signal to, as the external device, any sensor device 10 including the output unit 13 using the communication unit 21. In this case, the control unit 15 of the sensor device 10 receives the rating signal using the communication unit 21. The control unit 15 causes the output unit 13 as the notification unit to notify of what is indicated by the received rating signal. As an example of the notification, the control unit 15 causes the output unit 13 to output what is indicated by the rating signal. With this configuration, the user can understand ratings of states of body parts thereof during walking.

When the sensor device 10A is an earphone or included in an earphone, for example, the control unit 26 may transmit a rating signal to the earphone as the external device using the communication unit 21. In this case, the control unit 15 of the sensor device 10A receives the rating signal using the communication unit 11. The control unit 15 of the sensor device 10A causes the output unit 13 as the notification unit to notify of what is indicated by the rating signal. As an example of the notification, the control unit 15 of the sensor device 10A notifies of what is indicated by the rating signal by causing the speaker of the output unit 13 to output what is indicated by the rating signal as a sound. With this configuration, the user can be notified of ratings of states of body parts thereof using a sound. When the user is notified of ratings of states of body parts thereof using a sound, the user's walking is less likely to be interfered with.

The control unit 26 may notify, using the notification unit, the user of what is indicated by a generated rating signal. As an example of the notification, the control unit 26 may cause the output unit 23 to output what is indicated by a generated rating signal. As another example of the notification, the control unit 26 may cause the vibration unit 24 to vibrate in a vibration pattern based on determined ratings.

[Process for Selecting Learning Models]

The control unit 26 may select, from among a plurality of learning models, learning models to be used for the above-described process for determining ratings in accordance with types of sensor devices 10 that have transmitted sensor data to the electronic device 20. The control unit 26 may refer to the correspondences stored in the storage unit 25, such as those illustrated in FIG. 6, and select learning models to be used for the process for determining ratings.

The learning models illustrated in FIG. 6 have been generated by a method for generating a learning model, which will be described later. Values in parentheses shown beside each of the learning models are precision and accuracy of the learning model calculated in the method for generating a learning model, which will be described later. A method for calculating precision and accuracy of a learning model will be described later. A left value in parentheses is precision of a learning model. A right value in parentheses is accuracy of a learning model.

In FIG. 6, learning models with double circles are ones with a precision of 90% or higher and an accuracy of 70% or higher. Learning models with circles are ones that do not satisfy the conditions of the precision and accuracy of learning models with double circles. The learning models with circles are ones with a precision of 80% or higher and an accuracy of 60% or higher. Learning models with triangles are ones with a precision of lower than 80% or an accuracy of lower than 60%. The control unit 26 may determine ratings of a subset of (1) state of head to (5) state of feet or all of (1) state of head to (5) state of feet in accordance with precision and accuracy of learning models.

In FIG. 6, the control unit 26 selects case C1, case C2, case C3, case C4, or case C5 to select learning models to be used for the process for determining ratings. In cases C1 to C5, learning models to be used for the process for determining ratings and types of sensor devices 10 for obtaining feature data to be input to the learning models are associated with each other. The learning models, however, are not limited to those illustrated in FIG. 6. Learning models that employ sensor data or feature data obtained by sensor devices 10 combined together in any manner may be used.

The control unit 26 may select one of cases C1 to C5 in accordance with types of sensor devices 10 that are to transmit sensor data to the electronic device 20. In an example, the control unit 26 may select, from among a plurality of sensor devices 10 that has transmitted sensor data to the electronic device 20, any combination of sensor devices 10. The control unit 26 may select, from among cases C1 to C5, a case corresponding to the selected combination of sensor devices 10. Information regarding feature data to be used in cases C1 to C5, which will be described hereinafter, may be stored in the storage unit 25 while being associated with cases C1 to C5.

<Case C1>

When the sensor device 10 that transmits sensor data to the electronic device 20 is only the sensor device 10A, the control unit 26 may select case C1. When the sensor device 10 worn by the user is only the sensor device 10A, for example, the sensor device 10 that transmits sensor data to the electronic device 20 is only the sensor device 10A. When the sensor device 10A is selected from among a plurality of sensor devices 10 that has transmitted sensor data to the electronic device 20, too, the control unit 26 may select case C1.

In case C1, the control unit 26 selects learning models 30A, 30B, 30C, 30D, and 30E when determining ratings of (1) state of head, (2) state of arms, (3) state of trunk, (4) state of knees, and (5) state of feet, respectively.

In case C1, feature data input to the learning models 30A to 30E includes feature data indicating features of movement of the user's head in the up-and-down direction of the global coordinate system and feature data indicating features of movement of the user's head in the left-and-right direction of the global coordinate system. The feature data input to the learning models 30A to 30E, however, may just include feature data indicating features of movement of the user's head in at least the front-and-back direction, the left-and-right direction, or the up-and-down direction of the global coordinate system.

In case C1 according to the present embodiment, the control unit 26 inputs three pieces of feature data to each of the learning models 30A to 30E.

One of the three pieces of feature data input to the learning models 30A to 30E corresponds to the feature data indicating features of movement of the user's head in the up-and-down direction of the global coordinate system. In the present embodiment, this piece of feature data is an average of angles of the user's head in the up-and-down direction of the global coordinate system. This piece of feature data is obtained from sensor data indicating movement of the user's head detected by the sensor device 10A. The average of the angles of the user's head in the feature data may be an average of angles of the user's head in the user's gait cycle.

The other two of the three pieces of feature data input to the learning models 30A to 30E correspond to the feature data indicating features of movement of the user's head in the left-and-right direction of the global coordinate system. These two pieces of feature data are a maximum of angles of the user's head in the left-and-right direction of the global coordinate system and an average of the angles of the user's head in the left-and-right direction of the global coordinate system in the present embodiment. These two pieces of feature data are obtained from the sensor data indicating movement of the user's head detected by the sensor device 10A. The maximum and the average of the angles of the user's head in the feature data may be a maximum and an average of angles of the user's head in the user's gait cycle, respectively.

<Case C2>

When the sensor devices 10 that have transmitted sensor data to the electronic device 20 are only the sensor device 10A and the sensor device 10D, the control unit 26 may select case C2. When the sensor device 10A and the sensor device 10D are selected from among a plurality of sensor devices 10 that has transmitted sensor data to the electronic device 20, too, the control unit 26 may select case C2.

In case C2, the control unit 26 selects learning models 30F, 30G, 30H, 30I, and 30J when determining ratings of (1) state of head, (2) state of arms, (3) state of trunk, (4) state of knees, and (5) state of feet.

In case C2, feature data input to the learning models 30F to 30J includes, as in or similarly to case C1, feature data indicating features of movement of the user's head in the up-and-down direction of the global coordinate system and feature data indicating features of movement of the user's head in the left-and-right direction of the global coordinate system. Furthermore, the feature data input to the learning model 30F to 30J includes feature data indicating features of movement of one of the user's feet.

In case C2 according to the present embodiment, the control unit 26 inputs three pieces of feature data to each of the learning models 30F to 30J.

Two of the three pieces of feature data input to the learning models 30F to 30J correspond to the feature data indicating features of movement of the user's head in the up-and-down direction of the global coordinate system and the feature data indicating features of movement of the user's head in the left-and-right direction of the global coordinate system. These two pieces of feature data are an average of angles of the user's head in the up-and-down direction of the global coordinate system and a maximum of angles of the user's head in the left-and-right direction of the global coordinate system in the present embodiment. These two pieces of feature data are obtained from data indicating movement of the user's head detected by the sensor device 10A. The average and the maximum of the angles of the user's head in the feature data may be an average and a maximum of angles of the user's head in the user's gait cycle.

The other one of the three pieces of feature data input to the learning models 30F to 30J corresponds to the feature data indicating features of movement of the user's foot. This pieces of feature data is a maximum of acceleration of the user's foot in the up-and-down direction of the local coordinate system based on the position of the sensor device 10D in the present embodiment. This piece of feature data is obtained from sensor data indicating movement of the user's foot detected by the sensor device 10D. The maximum of the acceleration of the user's foot in the feature data may be a maximum of acceleration of the user's foot in the user's gait cycle.

<Case C3>

When the sensor devices 10 that have transmitted sensor data to the electronic device 20 are only the sensor device 10A and the sensor device 10C, the control unit 26 may select case C3. When the sensor device 10A and the sensor device 10C are selected from a plurality of sensor devices 10 that has transmitted sensor data to the electronic device 20, too, the control unit 26 may select case C3.

In case C3, the control unit 26 selects learning models 30K, 30L, 30M, 30N, and 30O when determining ratings of (1) state of head, (2) state of arms, (3) state of trunk, (4) state of knees, and (5) state of feet.

In case C3, feature data input to the learning models 30K to 30O includes, as in or similarly to case C1, feature data indicating features of movement of the user's head in the up-and-down direction of the global coordinate system and feature data indicating features of movement of the user's head in the left-and-right direction of the global coordinate system. Furthermore, the feature data input to the learning models 30K to 30O includes feature data indicating features of movement of one of the user's thighs.

In case C3 according to the present embodiment, the control unit 26 inputs three pieces of feature data to each of the learning models 30K to 30O.

Two of the three pieces of feature data input to the learning models 30K to 30O correspond to the feature data indicating features of movement of the user's head in the up-and-down direction of the global coordinate system and the feature data indicating features of movement of the user's head in the left-and-right direction of the global coordinate system. These two pieces of feature data are an average of angles of the user's head in the up-and-down direction of the global coordinate system and an average of angles of the user's head in the left-and-right direction of the global coordinate system in the present embodiment. These two pieces of feature data are obtained from sensor data indicating movement of the user's head detected by the sensor device 10A. The averages of the angles of the user's head in the feature data may be averages of angles of the user's head in the user's gait cycle.

The other one of the three pieces of feature data input to the learning models 30K to 30O is the feature data indicating features of movement of the user's thigh. This piece of feature data is a variance of angular velocity of the user's thigh in the left-and-right direction of the local coordinate system based on the position of the sensor device 10C in the stance phase in the present embodiment. This piece of feature data is obtained from sensor data indicating movement of the user's thigh detected by the sensor device 10D.

<Case C4>

When the sensor devices 10 that have transmitted sensor data to the electronic device 20 are only the sensor device 10A and the sensor device 10B, the control unit 26 may select case C4. When the sensor device 10A and the sensor device 10B are selected from a plurality of sensor devices 10 that has transmitted sensor data to the electronic device 20, too, the control unit 26 may select case C4.

In case C4, the control unit 26 selects learning models 30P, 30Q, 30R, 30S, and 30T when determining ratings of (1) state of head, (2) state of arms, (3) state of trunk, (4) state of knees, and (5) state of feet.

In case C4, the feature data input to the learning models 30P to 30T includes, as in or similarly to case C1, feature data indicating features of movement of the user's head in the up-and-down direction of the global coordinate system and feature data indicating features of movement of the user's head in the left-and-right direction of the global coordinate system. The feature data input to the learning models 30P to 30T also includes feature data indicating features of movement of one of the user's forearms.

In case C4 according to the present embodiment, the control unit 26 inputs three pieces of feature data to each of the learning models 30P to 30T.

Two of the three pieces of feature data input to the learning models 30P to 30T correspond to the feature data indicating features of movement of the user's head in the up-and-down direction of the global coordinate system and the feature data indicating features of movement of the user's head in the left-and-right direction of the global coordinate system. Theses two pieces of feature data are an average of angles of the user's head in the up-and-down direction of the global coordinate system and an angle of the user's head in the left-and-right direction of the global coordinate system at a landing time in the present embodiment. These two pieces of feature data are obtained from sensor data indicating movement of the user's head detected by the sensor device 10A. The average of the angles of the user's head in the feature data may be an average of angles of the user's head in the user's gait cycle.

The other one of the three pieces of feature data input to the learning models 30P to 30T corresponds to the feature data indicating features of movement of the user's forearm. This piece of feature data is a variance of acceleration of the user's forearm in the front-and-back direction of the local coordinate system based on the position of the sensor device 10B in the present embodiment. This piece of feature data is obtained from sensor data indicating movement of the user's forearm detected by the sensor device 10B. The variance of the acceleration of the user's forearm in the feature data may be a variance of acceleration of the user's forearm in the user's gait cycle.

<Case C5>

When the sensor devices 10 that have transmitted sensor data are only the sensor device 10A, the sensor device 10B, and the sensor device 10D, the control unit 26 may select case C5. When the sensor device 10A, the sensor device 10B, and the sensor device 10D are selected from among a plurality of sensor devices 10 that has transmitted sensor data to the electronic device 20, too, the control unit 26 may select case C5.

In case C5, the control unit 26 selects learning models 30U, 30V, 30W, 30X, and 30Y when determining ratings of (1) state of head, (2) state of arms, (3) state of trunk, (4) state of knees, and (5) state of feet.

In case C5, feature data input to the learning models 30U to 30Y includes, as in or similarly to case C1, feature data indicating features of movement of the user's head in the up-and-down direction of the global coordinate system and feature data indicating features of movement of the user's head in the left-and-right direction of the global coordinate system. The feature data input to the learning models 30U to 30Y also includes feature data indicating features of movement of one of the user's forearms and feature data indicating features of movement of one of the user's thighs.

In case C5 according to the present embodiment, the control unit 26 inputs four pieces of feature data to each of the learning models 30U to 30Y.

Two of the four pieces of feature data input to the learning models 30U to 30Y correspond to the feature data indicating features of movement of the user's head in the up-and-down direction of the global coordinate system and the feature data indicating features of movement of the user's head in the left-and-right direction of the global coordinate system. These two pieces of feature data are an average of angles of the user's head in the up-and-down direction of the global coordinate system and an angle of the user's head in the left-and-right direction of the global coordinate system at a landing time in the present embodiment. These two pieces of feature data are obtained from sensor data indicating movement of the user's head detected by the sensor device 10A. The average of the angles of the user's head in the feature data may be an average of angles of the user's head in the user's gait cycle.

One of the four pieces of feature data input to the learning models 30U to 30Y corresponds to the feature data indicating features of movement of the user's forearm. This piece of feature data is a maximum of acceleration of the user's forearm in the front-and-back direction of the local coordinate system based on the position of the sensor device 10B in the present embodiment. This piece of feature data is obtained from sensor data indicating movement of the user's forearm detected by the sensor device 10B. The maximum of the acceleration of the user's forearm in the feature data may be a maximum of acceleration of the user's forearm in the user's gait cycle.

The other one of the four pieces of feature data input to the learning models 30U and 30Y corresponds to the feature data indicating features of movement of the user's thigh. This piece of feature data is a maximum of acceleration of a corresponding one of the user's feet in the up-and-down direction of the local coordinate system based on the position of the sensor device 10D in the present embodiment. This piece of feature data is obtained from sensor data indicating movement of the user's thigh detected by the sensor device 10D. The maximum of the acceleration of the user's foot in the feature data may be a maximum of acceleration of the user's foot in the user's gait cycle.

[Method for Generating Learning Model]

The method for generating a learning model will be described hereinafter. In generation of a learning model, a subject walking database was used. As the subject walking database, data provided in "Yoshiyuki Kobayashi, Naoto Hida, Kanako Nakajima, Masahiro Fujimoto, and Masaaki Mochimaru, "2019: AIST Gait Database 2019", [Online], [Retrieved on May 24, 2021], Internet <https://unit.aist-.go.jp/harc/ExPART/GDB2019_e.html>" was used. Walking data regarding a plurality of subjects was registered in the walking database. The walking database regarding the subjects had been detected by a motion capture system and a floor reaction force gauge.

Walking of the subjects in the walking database was rated by an instructor who advised on walking. The instructor rated (1) state of head, (2) state of arms, (3) state of trunk, (4) state of knees, and (5) state of feet of the subjects during walking by giving scores of 1 to 5. The instructor rated walking of the subjects on the basis of the above-described interpretations of ways to walk generally considered good.

Feature data was obtained from data indicating movement of the subjects detected by the motion capture system. Datasets were generated by associating the feature data and the scores given by the instructor with each other. 980 datasets were generated using 10-pace walking data regarding 98 subjects. A learning model was generated through cross-validation based on the datasets. Among the 980 datasets, 800 datasets, which is 80% of the total, were used as datasets for training the learning model in the cross-validation. Among the 980 datasets, 180 datasets, which is 20% of the total, were used as datasets for rating the learning model. The 980 datasets were divided into 80% training datasets and 20% rating datasets by 10 different methods. The total number of trials was 846,000.

Precision and accuracy of the generated learning model were calculated. The precision and accuracy of the learning model were calculated on the basis of the number of correct and incorrect results of estimation performed by the learning model. In a determination whether a result of estimation performed by the learning model was correct or incorrect, scores were divided into three levels. More specifically, scores were divided into scores exceeding 3, scores that are 3, and scores lower than 3. The scores exceeding 3 were also expressed as "good". The scores that are 3 were also expressed as "average". The scores lower than 3 were also expressed as "poor". If a score of "good" or "poor" of the learning model matched a score of "good" or "poor" given by the instructor, a result of estimation performed by the learning model was determined to be correct. If a score of "good" or "poor" of the learning model did not match a score of "good" or "poor" given by the instructor, on the other hand, a result of estimation performed by the learning model was determined to be incorrect. If a score of the learning model was 3, a result of estimation performed by the learning model was determined to be neither correct nor incorrect.

The precision of the learning model was calculated by dividing the number of correct results of estimation by the sum of the number of corrects results of estimation and the number of incorrect results of estimation. For example, the precision of the learning model was calculated using expression (1).

$$\text{Precision of learning model} = (CR)/(CR+ICR) \quad \text{expression (1)}$$

In expression (1), CR denotes the number of correct results of estimation. ICR denotes the number of incorrect results of estimation.

The accuracy of the learning model was calculated by dividing the number of correct results of estimation by the total number of results of estimation. For example, the accuracy of the learning model was calculated using expression (2).

$$\text{Accuracy of learning model} = (CR)/(CR+ICR+NR) \quad \text{expression (2)}$$

In expression (2), CR denotes the number of correct results of estimation. ICR denotes the number of incorrect results of estimation. NR denotes the number of results of estimation performed by the learning model that are neither correct nor incorrect. That is, NR denotes the number of results where a score of the learning model was 3.

Here, the inventors set the minimum number of pieces of feature data to be input to each learning model to be 3, and searched for a combination of pieces of feature data that would increase ratings of the precision and accuracy of the learning model by changing the combination of pieces of feature data to be input to the learning model. The inventors obtained results illustrated in FIGS. 7 and 8.

FIG. 7 is a graph illustrating the precision of the learning models. FIG. 8 is a graph illustrating the accuracy of the learning models. Cases C1 to C5 illustrated in FIGS. 7 and 8 are the same as those described with reference to FIG. 6. FIGS. 7 and 8 illustrate the precision and accuracy of the learning models for (1) state of head to (5) state of feet.

As illustrated in FIG. 7, in case C1, the precision of the learning models was highest for (1) state of head among levels of precision for (1) state of head to (5) state of feet. As illustrated in FIG. 8, in case C1, the accuracy of the learning models was highest for (1) state of head among levels of accuracy for (1) state of head to (5) state of feet. In case C1, feature data input to the learning models is feature data indicating features of movement of a subject's (user's) head. The precision and accuracy of the learning models are considered to have been highest for (1) state of head among the levels of precision and accuracy for (1) state of head to (5) state of feet since the feature data indicating features of movement of the user's head was used in case C1.

As illustrated in FIG. 7, in case C1, the precision of the learning models for other than (1) state of head, namely (2) state of arms to (5) state of feet, was 80% or higher. As illustrated in FIG. 8, in case C1, the accuracy of the learning models for other than (1) state of head, namely (2) state of arms to (5) state of feet, was 50% or higher. As indicated by these results, states of body parts of the user other than the user's head can be rated with certain levels of precision on the basis of feature data indicating features of movement of the user's head.

Movement of the user's head in the up-and-down direction and the left-and-right direction of the global coordinate system reflects movement of body parts of the user other than the user's head during walking. If the user swings his/her arms or kicks the ground with his/her feet, for example, the user's body moves in the up-and-down direction and the left-and-right direction of the global coordinate system. When the user's body moves in the up-and-down direction and the left-and-right direction of the global coordinate system, the user's head moves in the up-and-down direction and the left-and-right direction of the global coordinate system.

Movement of the user's head in the up-and-down direction and the left-and-right direction of the global coordinate system thus reflects movement of body parts of the user other than the user's head during walking. States of body parts of the user other than the user's head during walking, therefore, are expected to be rated using feature data indicating features of movement of the user's head in the up-and-down direction and the left-and-right direction of the global coordinate system as feature data input to the learning model. As described above, in case C1, feature data indicating features of movement of the user's head in the up-and-down direction and the left-and-right direction of the global coordinate system is used as feature data input to the learning model. In case C1, states of body parts of the user other than the user's head are estimated to have been rated with certain levels of precision with this configuration.

As illustrated in FIG. 7, in case C2, the accuracy of the learning models for (1) state of head to (5) state of feet was higher than in case C1. In case C2, the precision of the learning models for (5) state of feet was higher than in cases C1, C3, and C4. As illustrated in FIG. 8, in case C2, the accuracy of the learning models for (1) state of head to (5) state of feet was higher than in case C1. In case C2, the accuracy of the learning models for (5) state of feet was higher than in cases C1 and C3.

In case C2, feature data indicating features of movement of more body parts of the user than in case C1 is used as feature data input to the learning models. For example, in case C2, as in or similarly to case C1, feature data indicating features of movement of the user's head in the up-and-down direction and the left-and-right direction of the global coordinate system is used as feature data. In case C2, feature data indicating features of movement of one of the user's feet is used in addition to these pieces of feature data. Since the feature data indicating features of movement of more body parts of the user than in case C1 is used in case C2, the precision and accuracy of the learning models for (1) state of head to (5) state of feet are estimated to have been higher than in case C1. Since the feature data indicating features of movement of the user's foot is used in case C2, the precision and accuracy of the learning model for (5) state of feet are estimated to have been higher than in case C1 and the like.

As illustrated in FIG. 7, in case C3, the precision of the learning models for (1) state of head to (5) state of feet was higher than in case C1. In case C3, the precision of the learning models for (4) state of thighs was higher than in cases C1, C2, and C4. As illustrated in FIG. 8, in case C3, the accuracy of the learning models for (1) state of head to (5) state of feet was higher than in case C1. In case C3, the accuracy of the learning models for (4) state of thighs was higher than in cases C1, C2, and C4.

In case C3, feature data indicating movement of more body parts of the user than in case C1 is used as feature data input to the learning models. For example, in case C3, as in or similarly to case C1, feature data indicating features movement of the user's head in the up-and-down direction and the left-and-right direction of the global coordinate system is used as feature data. In case C3, feature data indicating features of movement of one of the user's thighs is used in addition to these pieces of feature data. Since the feature data indicating features of movement of more body parts of the user than in case C1 is used in case C3, the precision and accuracy of the learning models for (1) state of head to (5) state of feet were higher than in case C1. Since the feature data indicating features of movement of the user's thigh is used in case C3, the precision and accuracy of the learning models for (4) state of thighs are estimated to have been higher than in case C1 and the like.

As illustrated in FIG. 7, in case C4, the precision of the learning models for (1) state of head to (5) state of feet was higher than in case C1. In case C4, the precision of the learning models for (2) state of arms was higher than in cases C1, C2, and C3. As illustrated in FIG. 8, in case C4, the accuracy of the learning models for (1) state of head to (5) state of feet was higher than in case C1. In case C4, the accuracy of the learning models for (2) state of arms was higher than in cases C1, C2, and C3.

In case C4, feature data indicating movement of more body parts of the user than in case C1 is used as feature data input to the learning models. For example, in case C4, as in or similarly to case C1, feature data indicating features of movement of the user's head in the up-and-down direction and the left-and-right direction of the global coordinate system is used as feature data. In case C4, feature data indicating features of movement of one of the user's forearms is used in addition to these pieces of feature data. Since the feature data indicating features of movement of more body parts of the user than in case C1 is used in case C4, the precision and accuracy of the learning models for (1) state of head to (5) state of feet are estimated to have been higher than in case C1. Since the feature data indicating features of movement of the user's forearm in case C4, the precision and accuracy of the learning model for (2) state of arms are estimated to have been higher than in case C1 and the like.

As illustrated in FIG. 7, in case C5, the precision of the learning models for (1) state of head to (5) state of feet was higher than in case C1. As illustrated in FIG. 8, in case C5, the accuracy of the learning models for (1) state of head to (5) state of feet was higher than in case C1.

In case C5, feature data indicating features of more body parts of the user than in cases C1 to C4 is used as feature data input to the learning models. Since the feature data indicating features of more body parts than in cases C1 to C4 is used in case C5, the precision and accuracy of the learning model for (1) state of head to (5) state of feet are estimated to have been higher than in case C1. Since the feature data indicating features of more body parts of the user than in cases C1 to C4 is used in case C5, the precision and accuracy of the learning model for (1) state of head to (5) state of feet are estimated to have been higher than in case C1.

(Operations of System)

FIG. 9 is a flowchart illustrating operations included in a rating process performed by the electronic device 20 illustrated in FIG. 1. The operations correspond to an example of a method for processing information according to the present embodiment. The control unit 26 receives an input for requesting execution of walking rating using the input unit 22, for example, and starts the rating process with processing in step S10.

The control unit 26 receives the input for requesting execution of walking rating using the input unit 22 (step S10). A user who wears the sensor devices 10 makes the input from the input unit 22.

The control unit 26 transmits, using the communication unit 21, a signal for requesting a start of data detection to the sensor devices 10 as a broadcast signal (step S11). After the processing in step S11 is performed, at least one of the sensor devices 10 transmits sensor data to the electronic device 20.

The control unit 26 receives, from the at least one of the sensor devices 10, the sensor data using the communication unit 21 (step S12).

The control unit 26 refers to correspondences such as those illustrated in FIG. 6 and selects, from among a plurality of learning models, learning models corresponding to types of sensor devices 10 that have transmitted the sensor data to the electronic device 20 (step S13).

The control unit 26 obtains feature data from the sensor data received in the processing in step S12 (step S14). The control unit 26 inputs the feature data obtained in the processing in step S14 to the learning models selected in the processing in step S13 to obtain scores such as those illustrated in FIG. 5 (step S15). After obtaining the scores, the control unit 26 determines ratings of states of body parts corresponding to the scores.

The control unit 26 generates a rating signal based on the determined ratings (step S16). The control unit 26 transmits, using the communication unit 21, the rating signal generated in the processing in step S16 to an external device (step S17). After performing the processing in step S17, the control unit 26 ends the rating process.

After ending the rating process, the control unit 26 may perform the rating process again if the user walks a set number of paces. The user may input in advance the set number of paces from the input unit 22. In a second rating process, the control unit 26 may begin the process with the processing in step S11. The control unit 26 may repeatedly perform the rating process each time the user walks the set number of paces until the control unit 26 receives an input for requesting an end of the rating process from the input unit 22. The user, for example, makes the input for requesting an end of the rating process from the input unit 22. The user makes the input for requesting an end of the rating process from the input unit 22 after, for example, the user stops walking.

In the electronic device 20 as the information processing apparatus, the control unit 26 can thus estimate, using learning models, states of body parts of the user other than body parts of the user to which the sensor devices 10 are attached. As described above, when estimating the states of the body parts of the user other than the body parts of the user to which the sensor device 10 is attached, for example, the control unit 26 can determine ratings of the body parts. For example, the control unit 26 can select case C1 illustrated in FIG. 6 and determine ratings of (2) state of arms to (5) state of feet, which are different from the user's head, to which the sensor device 10A is attached. With this configuration, in the present embodiment, not only states of body parts of the user to which the sensor devices 10 are attached but also states of other body parts of the user can be estimated.

During these years, walking is gaining attention as an easy exercise. A walking user, however, needs to pay attention to obstacles ahead or around. Since a walking user needs to pay attention to obstacles ahead or around, he/she might not be able to pay attention to his/her own posture. When a walking user is not able to pay attention to his/her own posture, he/she might walk in an incorrect posture without realizing it. If a user walks in an incorrect posture, an exercise effect of walking might decrease. Since walking is often a familiar exercise for a user, the user often finds it difficult to correct his/her own posture during walking.

As described above, in the electronic device 20 according to the present embodiment, the control unit 26 can estimate states of body parts of the user. With this configuration, the user can be given an opportunity to correct his/her own posture during walking. Since the user is given an opportunity to correct his/her own posture, the user can walk in a correct posture. Since the user can walk in a correct posture, an exercise effect of walking increases.

According to the present embodiment, therefore, a novel technique for estimating states of body parts of the user during walking is provided.

Furthermore, the control unit 26 may estimate states of more body parts of the user than body parts of the user to which the sensor devices 10 are attached. N (N is an integer larger than or equal to 1) sensor devices 10, for example, are assumed to be attached to the user. In this case, the control unit 26 may obtain N pieces of sensor data from the N sensor devices 10 and determine ratings of states of (N+1) or more body parts of the user.

For example, N is assumed to be 1 and the sensor device 10A is assumed to be attached to the user. In this case, the control unit 26 obtains one piece of sensor data from the sensor device 10A. The control unit 26 selects case C1 illustrated in FIG. 6 and determines ratings of states of two or more body parts, namely states of five body parts consisting of (1) state of head to (5) state of feet, for example, on the basis of the obtained piece of sensor data.

In another example, N is assumed to be 2 and the sensor device 10A and the sensor device 10D are assumed to be attached to the user. In this case, the control unit 26 obtains two pieces of sensor data from the sensor device 10A and sensor device 10D, respectively. The control unit 26 selects case C2 illustrated in FIG. 6 and determines ratings of states of three or more body parts, that is, states of five body parts consisting of (1) state of head to (5) state of feet, for example, on the basis of the obtained two pieces of sensor data.

Since states of more body parts of the user than body parts to which the sensor devices 10 are attached are estimated, the electronic device 20 excels in convenience for the user.

The at least one sensor device 10 included in the information processing system 1 may include the sensor device 10A attached to the user's head. The control unit 26 may obtain sensor data indicating movement of the user's head from the sensor device 10A. In this case, the control unit 26 may select case C1 illustrated in FIG. 6. That is, feature data may include feature data indicating features of movement of the user's head in the up-and-down direction of the user, that is, the up-and-down direction of the global coordinate, and feature data indicating features of movement of the user's head in the left-and-right direction of the user, that is, the left-and-right direction of the global coordinate system. With this configuration, even when the sensor device 10 worn by the user is only the sensor device 10A, ratings of states of body parts of the user can be determined. That is, the user may just wear only the sensor device 10A. As a result, the convenience for the user improves. When the sensor device 10A is an earphone or included in an earphone, the user can easily wear the sensor device 10A on his/her head. Since the user can easily wear the sensor device 10A on his/her head, the convenience for the user further improves. Since only sensor data detected by the sensor device 10A is used, times at which the sensor devices 10 detect data need not be synchronized with each other. Since the times at which the sensor devices 10 detect data need not be synchronized with each other, ratings of states of body parts of the user can be determined more easily.

The at least one sensor device 10 included in the information processing system 1 may include the sensor device 10A attached to the user's head and the sensor device 10D attached to one of the user's feet. The control unit 26 may obtain sensor data indicating movement of the user's head from the sensor device 10A and sensor data indicating movement of the user's foot from the sensor device 10D. In this case, the control unit 26 may select case C2 illustrated in FIG. 6. That is, feature data may include feature data indicating features of movement of the user's head in the up-and-down direction of the global coordinate system, feature data indicating features of movement of the user's head in the left-and-right direction of the global coordinate system, and feature data indicating features of movement of the user's foot. As described above with reference to FIGS. 7 and 8, the precision and accuracy of the learning models for (1) state of head to (5) state of feet in case C2 were higher than in case C1. The control unit 26, therefore, can determine ratings of states of body parts of the user more precisely. When the sensor device 10A is an earphone or included in an earphone, the user can easily wear the sensor device 10A on his/her head. When the sensor device 10D is a wearable device of a shoe type, the user can easily wear the sensor device 10D on one of his/her feet. The convenience for the user, therefore, improves.

The at least one sensor device 10 included in the information processing system 1 may include the sensor device 10A attached to the user's head and the sensor device 10C attached to one of the user's thighs. The control unit 26 may obtain sensor data indicating movement of the user's head from the sensor device 10A and data indicating movement of the user's thigh from the sensor device 10D. In this case, the control unit 26 may select case C3 illustrated in FIG. 6. That is, feature data may include feature data indicating features of movement of the user's head in the up-and-down direction of the global coordinate system, feature data indicating features of movement of the user's head in the left-and-right direction of the global coordinate system, and feature data indicating features of movement of the user's thigh. As described above with reference to FIGS. 7 and 8, the precision and accuracy for (1) state of head to (5) state of feet in case C3 were higher than in case C1. The control unit 26, therefore, can determine ratings of states of body parts of the user more precisely. When the sensor device 10A is an earphone or included in an earphone, the user can easily wear the sensor device 10A on his/her head. With this configuration, the convenience for the user improves.

The at least one sensor device 10 included in the information processing system 1 may include the sensor device 10A attached to the user's head and the sensor device 10B attached to one of the user's forearms. The control unit 26 may obtain sensor data indicating movement of the user's head from the sensor device 10A and sensor data indicating movement of the user's forearm from the sensor device 10B. In this case, the control unit 26 may select case C4 illustrated in FIG. 6. That is, feature data may include feature data indicating features of movement of the user's head in the up-and-down direction of the global coordinate system, feature data indicating features of movement of the user's head in the left-and-right direction of the global coordinate system, and feature data indicating features of movement of the user's forearm. As described above with reference to FIGS. 7 and 8, the precision and accuracy for (1) state of head to (5) state of feet in case C4 were high. The control unit 26, therefore, can determine ratings of states of body parts of the user more precisely. When the sensor device 10A is earphones or included in earphones, the user can easily wear the sensor device 10A on his/her head. When the sensor device 10B is a wearable device of a wristwatch type, the user can easily wear the sensor device 10B on one of his/her forearms. With this configuration, convenience for the user improves.

The at least one sensor device 10 included in the information processing system 1 may include the sensor device 10A attached to the user's head, the sensor device 10B attached to one of the user's forearms, and the sensor device 10D attached to one of the user's feet. The control unit 26 may obtain sensor data indicating movement of the user's head from the sensor device 10A, sensor data indicating movement of the user's forearm from the sensor device 10B, and sensor data indicating movement of the user's foot from the sensor device 10D. In this case, the control unit 26 may select case C5 illustrated in FIG. 6. That is, feature data may include feature data indicating features of movement of the user's head in the up-and-down direction of the global coordinate system and feature data indicating features of movement of the user's head in the left-and-right direction of the global coordinate system. The feature data may also include feature data indicating features of movement of the user's forearm and feature data indicating features of one of the user's thighs. As described above with reference to FIGS. 7 and 8, the precision and accuracy for (1) state of head to (5) state of feet in case C5 were higher than in case C1. The control unit 26, therefore, can determine ratings of states of body parts of the user more precisely.

(Configuration of Another System)

FIG. 10 is a functional block diagram illustrating configuration of an information processing system 101 according to another embodiment of the present disclosure.

The information processing system 101 includes the sensor device 10, the electronic device 20, and a server 40. In the information processing system 101, the server 40 functions as an information processing apparatus and estimates states of body parts of the user.

The electronic device 20 and the server 40 are communicable with each other over the network 2. The network 2 may be any network such as a mobile communication network or the Internet.

As with or similarly to the information processing system 1, the control unit 26 of the electronic device 20 receives sensor data from the sensor device 10 using the communication unit 21. In the information processing system 101, the control unit 26 transmits sensor data to the server 40 over the network 2 using the communication unit 21.

The server 40 is, for example, a server belonging to a cloud computing system or another computing system. The server 40 includes a communication unit 41, a storage unit 42, and a control unit 43.

The communication unit 41 includes at least one communication module connectable to the network 2. The communication module is, for example, a communication module that complies with a standard for wired LAN (local area network), a wireless LAN, or the like. The communication unit 41 is connected to the network 2 over a wired LAN or a wireless LAN using the communication module.

The storage unit 42 includes at least one semiconductor memory, at least one magnetic memory, at least one optical memory, or a combination of at least two of these. The semiconductor memory is, for example, a RAM, a ROM, or the like. The RAM is, for example, an SRAM, a DRAM, or the like. The ROM is, for example, an EEPROM or the like. The storage unit 42 may function as a main storage device, an auxiliary storage device, or a cache memory. The storage unit 42 stores data used for operation of the server 40 and data obtained as a result of the operation of the server 40. For example, the storage unit 42 stores a system program, application programs, embedded software, and the like. For example, the storage unit 42 stores learning models, correspondences such as those illustrated in FIG. 6, and the like.

The control unit 43 includes at least one processor, at least one dedicated circuit, or a combination of these. The processor is a general-purpose processor such as a CPU or a GPU or a dedicated processor specialized in a certain type of processing. The dedicated circuit is, for example, an FPGA, an ASIC, or the like. The control unit 43 performs processing relating to the operation of the server 40 while controlling the components of the server 40.

The control unit 43 receives sensor data from the electronic device 20 over the network 2 using the communication unit 41. The control unit 43 estimates states of body parts of the user on the basis of sensor data by performing a process that is the same as or similar to that performed by the control unit 26 of the electronic device 20.

(Operations of Another System)

FIG. 11 is a sequence diagram illustrating operations included in a rating process performed by the information processing system 101 illustrated in FIG. 10. These operations correspond to an example of a method for processing information according to the present embodiment. The electronic device 20 receives an input for requesting execution of walking rating, and the information processing system 101 starts the rating process with processing in step S20. In the following description, learning models are assumed to have been subjected to machine learning such that when feature data is input, scores are output.

The control unit 26 of the electronic device 20 receives, using the input unit 22, the input for requesting executing of walking rating (step S20). The control unit 26 transmits, using the communication unit 21, a signal for requesting a start of data detection to a plurality of sensor devices 10 as a broadcast signal (step S21).

The control unit 15 of the sensor device 10 receives the signal for requesting a start of data detection from the electronic device 20 using the communication unit 11 (step S22). Upon receiving the signal, the control unit 15 starts the data detection. The control unit 15 obtains data detected by the sensor unit 12 from the sensor unit 12 and transmits, using the communication unit 11, the obtained data to the electronic device 20 as sensor data (step S23).

The control unit 26 of the electronic device 20 receives the sensor data from the sensor device 10 using the communication unit 21 (step S24). The control unit 26 transmits the sensor data to the server 40 over the network 2 using the communication unit 21 (step S25).

The control unit 43 of the server 40 receives the sensor data from the electronic device 20 over the network 2 using the communication unit 41 (step S26). The control unit 43 selects, from among the plurality of learning models, learning models corresponding to a type of sensor device 10 that has transmitted the sensor data to the server 40 through the electronic device 20 (step S27). The control unit 43 obtains feature data from the sensor data received in the processing in step S26 (step S28). The control unit 43 obtains scores from the learning models selected in the processing in step S27 by inputting the feature data obtained in the processing in step S28 to the learning models (step S29). After obtaining the scores, the control unit 43 determines ratings of states of parts corresponding to the scores.

The control unit 43 of the server 40 generates a rating signal based on the determined ratings (step S30). The control unit 43 transmits the rating signal generated in the processing in step S30 to the electronic device 20 as an external device over the network 2 using the communication unit 41 (step S31).

The control unit 26 of the electronic device 20 receives the rating signal from the server 40 over the network 2 using the communication unit 21 (step S32). The control unit 26 causes the notification unit to notify of what is indicated by the rating signal (step S33). As an example of the notification, the control unit 26 may cause the output unit 23 to output what is indicated by the rating signal. As another example of the notification, the control unit 26 may cause the vibration unit 24 to vibrate in a vibration pattern based on the rating signal. As yet another example of the notification, the control unit 26 may transmit the rating signal to the sensor device 10 using the communication unit 21 and cause the sensor device 10 to notify of what is indicated by the rating signal. In this case, the control unit 15 of the sensor device 10 may cause the output unit 13 as the notification unit to output what is indicated by the rating signal. When the sensor device 10A receives the rating signal, the control unit 15 of the sensor device 10A may cause the speaker of the output unit 13 to output what is indicated by the rating signal as a sound.

After performing the processing in step S33, the information processing system 101 ends the rating process.

After ending the rating process, the information processing system 101 may perform the rating process again if the user walks the set number of paces. In a second rating process, the information processing system 101 may begin the process with the processing in step S23. The information processing system 101 may repeatedly perform the rating process each time the user walks the set number of paces until the electronic device 20 receives an input for requesting an end of the rating process from the input unit 22.

The information processing system 101 can produce effects that are the same as or similar to those produced by the information processing system 1.

Although embodiments of the present disclosure has been described on the basis of the drawings and examples, those skilled in the art can make various variations and alterations on the basis of the present disclosure. The scope of the present disclosure, therefore, also includes such variations and alterations. The functions of the components, for example, may be rearranged insofar as no contradiction is caused, and a plurality of components or the like may be combined together or further divided.

For example, learning models may be trained such that when sensor data or feature data is input, information regarding states of body parts of the user other than body parts of the user to which the sensor devices 10 are attached is output. In this case, the control unit 26 estimates, using the sensor data and the learning models, the states of the body parts of the user other than the body parts of the user to which the sensor devices 10 are attached.

For example, the feature data input to the learning models is not limited to those described above. As indicated by the results illustrated in FIGS. 7 and 8, for example, as the number of body parts of the user to which sensor devices 10 are attached increases, the number of types of feature data indicating features of movement of body parts increases, and precision and accuracy of the learning models increase. In order to increase the precision and accuracy of the learning models, therefore, the number of pieces of feature data input to the learning models may be increased by increasing the number of sensor devices 10 attached to body parts of the user.

For example, the electronic device 20 may be a wearable device of a glasses type. In this case, the output unit 23 may include a projector that projects an image onto lenses of the glasses. The control unit 26 may cause the output unit 23 to output determined ratings of states of body parts as an image. The image may include, for example, an image indicating ideal movement of a body part rated low among the body parts of the user.

For example, the rating threshold may be set on the basis of the user's age and gender or the like. In this case, the praise for the user and the advice may be set on the basis of the user's age and gender or the like.

For example, the storage unit 25 of the electronic device 20 may store learning models for different pieces of body data with which physical features of a plurality of users can be distinguished from one another. The body data includes, for example, at least one selected from the group consisting of age, gender, height, and weight. In this case, the control unit 26 receives an input indicating the body data regarding the user from the input unit 22. The control unit 26 may select, from among the plurality of learning models stored in the storage unit 25, learning models corresponding to the received body data regarding the user. With this configuration, states of body parts that suit body data regarding an individual can be rated.

For example, the storage unit 42 of the server 40 may store a learning model for each piece of body data. In this case, the control unit 26 of the electronic device 20 may receive an input indicating body data regarding the user from the input unit 22. Upon receiving the input indicating body data regarding the user, the control unit 26 of the electronic device 20 may transmit a signal indicating the body data regarding the user to the server 40 over the network 2 using the communication unit 21. The control unit 43 of the server 40 receives the signal indicating the body data regarding the user from the electronic device 20 over the network 2 using the communication unit 41. The control unit 43 of the server 40 may select, from among the plurality of learning models stored in the storage unit 42, a learning model corresponding to the body data regarding the user on the basis of the received signal indicating the body data regarding the user. With this configuration, states of body parts that suit body data regarding an individual can be rated.

For example, the control unit 26 of the electronic device 20 or the control unit 43 of the server 40 may calculate rhythm of the user's body movement, the user's stride, and the user's walking speed on the basis of sensor data. The control unit 26 of the electronic device 20 or the control unit 43 of the server 40 may calculate the user's walking time, which is time for which the user has walked, on the basis of sensor data. The control unit 26 of the electronic device 20 or the control unit 43 of the server 40 may calculate a walking distance, which is a distance over which the user has walked, on the basis of sensor data. If the walking time exceeds a time threshold or the walking distance exceeds a distance threshold, the control unit 26 of the electronic device 20 or the control unit 43 of the server 40 may generate a signal for urging the user to take a break or a signal for urging the user to stop walking. The control unit 26 of the electronic device 20 may transmit the generated signal to the above-described external device using the communication unit 21. The control unit 43 of the server 40 may transmit the generated signal to the electronic device 20 or the sensor device 10 over the network 2 using the communication unit 41. The time threshold may be set on the basis of an average walking time of general users or the like. The distance threshold may be set on the basis of an average distance over which general users walk at a time.

For example, the communication unit 21 of the electronic device 20 may include at least one reception module corresponding to a satellite positioning system. The reception module is, for example, a reception module compatible with a GPS (global positioning system). The reception module, however, is not limited to this. The reception module may be a reception module compatible with any satellite positioning system. In this case, the storage unit 25 may store map data. The control unit 26 may obtain positional information regarding the user using the communication unit 21. The control unit 26 may cause the output unit 23 to output the positional information regarding the user and the map data.

For example, the communication unit 11 of the sensor device 10 may also include at least one communication module connectable to the network 2 illustrated in FIG. 10. The communication module is a communication module that complies with a mobile communication standard such as LTE, 4G, or 5G. In this case, in the information processing system 101 illustrated in FIG. 10, the control unit 15 of the sensor device 10 may transmit data detected by the sensor device 10 to the server 40 over the network 2 using the communication unit 11.

For example, in the above-described embodiment, the control unit 26 of the electronic device 20 may estimate an overall state of two or more body parts of the user. The control unit 26 of the electronic device 20 or the control unit 43 of the server, however, may determine an overall state of two or more of (1) state of head, (2) state of arms, (3) state of trunk, (4) state of knees, and (5) state of feet.

For example, an embodiment where a general-purpose computer functions as the electronic device 20 according to the present embodiment is also possible. More specifically, a program where processing for achieving the functions of the electronic device 20 according to the present embodiment is described is stored in a memory of the general-purpose computer and read and executed by a processor. The configuration according to the present embodiment, therefore, can be achieved by a program executable by a processor or a non-transitory computer-readable medium storing the program.

REFERENCE SIGNS 1, 101 information processing system
2 network
10, 10A, 10B, 10C, 10D sensor device
11 communication unit
12 sensor unit
13 output unit
14 storage unit
15 control unit
20 electronic device
21 communication unit
22 input unit
23 output unit
24 vibration unit
25 storage unit
26 control unit
30, 30A to 30E, 30F to 30J, 30K to 30O, 30P to 30T, 30U to 30Y learning model
31 input layer
32 hidden layer
33 hidden layer
34 output layer
40 server
41 communication unit
42 storage unit
43 control unit

The invention claimed is:

1. An information processing apparatus comprising:
a controller is configured to:
obtain sensor data indicating movement of body parts of a user from at least one sensor device attached to the body parts of the user; and
estimate, on a basis of the sensor data and learning models, states of body parts of the user other than the body parts of the user to which the at least one sensor device is attached,
wherein, when the sensor data is input to the learning models, the learning models estimate states of body parts of the user other than the body parts of the user to which the at least one sensor device is attached, and
wherein the controller is further configured to select, from among the learning models, learning models for obtaining information regarding ratings in accordance with a type of sensor device that has transmitted the sensor data to the information processing apparatus.

2. The information processing apparatus according to claim 1,
wherein the controller is configured to estimate, on the basis of the learning models, states of more body parts of the user than a number of body parts of the user to which the at least one sensor device is attached.

3. The information processing apparatus according to claim 1,
wherein, when estimating the states of the body parts of the user, the controller obtains the information regarding the ratings from the learning models and determines ratings of the states of the body parts of the user.

4. The information processing apparatus according to claim 3,
wherein the controller is further configured to determine a rating of at least one selected from the group consisting of a state of the user's head, a state of the user's arms, a state of the user's trunk, a state of the user's knees, and a state of the user's feet.

5. The information processing apparatus according to claim 3, further comprising:
a communication unit,
wherein the controller is configured to generate a rating signal based on at least one of the ratings, and
wherein the communication unit is configured to transmit the generated rating signal to an external device.

6. The information processing apparatus according to claim 5,
wherein the external device is an earphone.

7. The information processing apparatus according to claim 1,
wherein, when feature data indicating features of movement of the body parts of the user to which the at least one sensor device is attached is input to the learning models, the learning models output information regarding ratings of the states of the body parts of the user other than the body parts of the user to which the at least one sensor device is attached, and
wherein the controller is configured to:
obtain the feature data from the sensor data; and
when estimating the states of the body parts of the user, obtains the information regarding the ratings from the learning models and determines the ratings of the states of the body parts of the user.

8. The information processing apparatus according to claim 7,
wherein the at least one sensor device includes a sensor device attached to the user's head,
wherein the controller is configured to obtain the sensor data indicating movement of the user's head, and
wherein the feature data includes data indicating features of movement of the user's head in a front-and-back direction, a left-and-right direction, and an up-and-down direction of the user.

9. The information processing apparatus according to claim 8,
wherein the feature data includes data indicating the features of the movement of the user's head in the up-and-down direction of the user and data indicating the features of the movement of the user's head in the left-and-right direction.

10. The information processing apparatus according to claim 9,
wherein the at least one sensor device further includes a sensor device attached to one of the user's feet,
wherein the controller is also configured to obtain the sensor data indicating movement of the user's foot, and
wherein the feature data further includes data indicating features of the movement of the user's foot.

11. The information processing apparatus according to claim 9,
wherein the at least one sensor device further includes a sensor device attached to one of the user's thighs,
wherein the controller is also configured to obtain the sensor data indicating movement of the user's thigh, and
wherein the feature data further includes data indicating the features of the movement of the user's thigh.

12. The information processing apparatus according to claim 9,
wherein the at least one sensor device further includes a sensor device attached to one of the user's forearms,
wherein the controller is also configured to obtain the sensor data indicating movement of the user's forearm, and
wherein the feature data further includes data indicating features of the movement of the user's forearm.

13. The information processing apparatus according to claim 9,
wherein the at least one sensor device further includes a sensor device attached to one of the user's forearms and a sensor device attached to one of the user's feet,
wherein the controller is also configured to obtain the sensor data indicating movement of the user's forearm and the sensor data indicating movement of the user's foot, and
wherein the feature data further includes data indicating features of the movement of the user's forearm and feature data indicating features of the movement of the user's foot.

14. An electronic device comprising:
a notification unit is configured to notify of information regarding the states of the body parts estimated by the information processing apparatus according to claim 1.

15. An information processing system comprising:
at least one sensor device configured to be attached to body parts of a user; and
an information processing apparatus configured to:
obtain sensor data indicating movement of the body parts from the at least one sensor device; and
estimate, on a basis of the obtained sensor data and learning models, states of body parts of the user other than the body parts of the user to which the at least one sensor device is attached,
wherein, when the sensor data is input to the learning models, the learning models estimate states of body parts of the user other than the body parts of the user to which the at least one sensor device is attached, and
wherein the information processing apparatus is further configured to select, from among the learning models, learning models for obtaining information regarding ratings in accordance with a type of sensor device that has transmitted the sensor data to the information processing apparatus.

16. A method for processing information, the method comprising:
obtaining sensor data indicating movement of body parts of a user from at least one sensor device attached to the body parts of the user; and
estimating, on a basis of the obtained sensor data and learning models, states of body parts of the user other than the body parts of the user to which the at least one sensor device is attached,
wherein, when the sensor data is input to the learning models, the learning models estimate states of body parts of the user other than the body parts of the user to which the at least one sensor device is attached, and
wherein the method further includes selecting, from among the learning models, learning models for obtaining information regarding ratings in accordance with a type of sensor device that has transmitted the sensor data.

17. A non-transitory computer readable medium storing a program that causes a computer to execute a process comprising:
obtaining sensor data indicating movement of body parts of a user from at least one sensor device attached to the body parts of the user; and
estimating, on a basis of the obtained sensor data and learning models, states of body parts of the user other than the body parts of the user to which the at least one sensor device is attached,
wherein, when the sensor data is input to the learning models, the learning models estimate states of body parts of the user other than the body parts of the user to which the at least one sensor device is attached, and
wherein the process further includes selecting, from among the learning models, learning models for obtaining information regarding ratings in accordance with a type of sensor device that has transmitted the sensor data.

\* \* \* \* \*